(12) United States Patent
Lannan et al.

(10) Patent No.: US 12,409,272 B2
(45) Date of Patent: Sep. 9, 2025

(54) PREFILLED SYRINGE WITH BREAKAWAY FORCE FEATURE

(71) Applicant: Antares Pharma, Inc., Ewing, NJ (US)

(72) Inventors: James W. Lannan, Brooklyn Center, MN (US); Julius C. Sund, Plymouth, MN (US)

(73) Assignee: Antares Pharma, Inc., Ewing, NJ (US)

( * ) Notice: Subject to any disclaimer, the term of this patent is extended or adjusted under 35 U.S.C. 154(b) by 262 days.

(21) Appl. No.: 18/169,774

(22) Filed: Feb. 15, 2023

(65) Prior Publication Data
US 2023/0191031 A1 Jun. 22, 2023

Related U.S. Application Data

(63) Continuation of application No. 16/591,169, filed on Oct. 2, 2019, now Pat. No. 11,602,597, which is a
(Continued)

(51) Int. Cl.
*A61B 5/20* (2006.01)
*A61M 5/20* (2006.01)
(Continued)

(52) U.S. Cl.
CPC ............ *A61M 5/2033* (2013.01); *A61M 5/50* (2013.01); *A61M 2005/2013* (2013.01); *A61M 2005/2073* (2013.01); *A61M 2005/3267* (2013.01)

(58) Field of Classification Search
CPC .. A61M 2005/2013; A61M 2005/2073; A61M 2005/3267; A61M 5/2033; A61M 5/50
See application file for complete search history.

(56) References Cited

U.S. PATENT DOCUMENTS

| 3,688,765 A | 9/1972 | Gasaway |
| 3,712,301 A | 1/1973 | Sarnoff |

(Continued)

FOREIGN PATENT DOCUMENTS

| AR | 00081651 | 10/2012 |
| AR | 082053 | 11/2012 |

(Continued)

OTHER PUBLICATIONS

Office Action for Korean Patent Application No. 10-2014-7027887 dated Mar. 8, 2016, 7 pages.
(Continued)

*Primary Examiner* — Deanna K Hall
(74) *Attorney, Agent, or Firm* — Morgan, Lewis & Bockius LLP

(57) ABSTRACT

A jet injector that includes a prefilled syringe. The syringe includes a fluid chamber that contains a medicament. The syringe also has an injection-assisting needle, and a plunger is movable within the fluid chamber. A housing is configured for allowing insertion of the needle to a penetration depth. The housing includes a retractable guard and an interference component, e.g., a lock ring, adjacent to the retractable guard that interferes with the movement of the retractable guard. An energy source is configured for biasing the plunger to produce an injecting pressure to jet inject the medicament from the fluid chamber through the needle to an injection site.

21 Claims, 11 Drawing Sheets

Related U.S. Application Data continuation of application No. 14/702,275, filed on May 1, 2015, now Pat. No. 10,478,559, which is a continuation of application No. 13/785,582, filed on Mar. 5, 2013, now Pat. No. 9,486,583.

(60) Provisional application No. 61/607,339, filed on Mar. 6, 2012.

(51) Int. Cl.
*A61M 5/50* (2006.01)
*A61M 5/32* (2006.01)

(56) References Cited

U.S. PATENT DOCUMENTS

| | | |
|---|---|---|
| 3,797,489 A | 3/1974 | Sarnoff |
| 3,882,863 A | 5/1975 | Sarnoff et al. |
| 4,484,910 A | 11/1984 | Sarnoff et al. |
| 4,558,690 A | 12/1985 | Joyce |
| 4,624,660 A | 11/1986 | Mijers et al. |
| 4,661,098 A | 4/1987 | Bekkering et al. |
| 4,664,653 A | 5/1987 | Sagstetter et al. |
| 4,678,461 A | 7/1987 | Mesa |
| 4,820,286 A | 4/1989 | van der Wal |
| 4,822,340 A | 4/1989 | Kamstra |
| 4,986,816 A | 1/1991 | Steiner et al. |
| 5,042,977 A | 8/1991 | Bechtold et al. |
| 5,078,680 A | 1/1992 | Sarnoff |
| 5,085,641 A | 2/1992 | Sarnoff et al. |
| 5,085,642 A | 2/1992 | Sarnoff et al. |
| 5,092,842 A | 3/1992 | Bechtold et al. |
| 5,102,393 A | 4/1992 | Sarnoff et al. |
| 5,114,406 A | 5/1992 | Gabriel et al. |
| 5,163,907 A | 11/1992 | Szuszkiewicz |
| 5,176,643 A | 1/1993 | Kramer et al. |
| 5,180,370 A | 1/1993 | Gillespie |
| 5,195,983 A | 3/1993 | Boese |
| 5,271,744 A | 12/1993 | Kramer et al. |
| 5,279,543 A | 1/1994 | Glikfeld et al. |
| 5,300,030 A | 4/1994 | Crossman et al. |
| 5,342,308 A | 8/1994 | Boschetti |
| 5,354,286 A | 10/1994 | Mesa et al. |
| 5,358,489 A | 10/1994 | Wyrick |
| 5,391,151 A | 2/1995 | Wilmot |
| 5,425,715 A | 6/1995 | Dalling et al. |
| 5,478,316 A | 12/1995 | Bitdinger et al. |
| 5,514,097 A | 5/1996 | Knauer |
| 5,540,664 A | 7/1996 | Wyrick |
| 5,567,160 A | 10/1996 | Massino |
| 5,569,192 A | 10/1996 | van der Wal |
| 5,593,388 A | 1/1997 | Phillips |
| 5,599,302 A | 2/1997 | Lilley et al. |
| 5,658,259 A | 8/1997 | Pearson et al. |
| 5,665,071 A | 9/1997 | Wyrick |
| 5,681,291 A | 10/1997 | Galli |
| 5,695,472 A | 12/1997 | Wyrick |
| 5,820,602 A | 10/1998 | Kovelman et al. |
| 5,836,911 A | 11/1998 | Marzynski et al. |
| 5,843,036 A | 12/1998 | Olive et al. |
| 5,851,197 A | 12/1998 | Marano et al. |
| 5,891,085 A | 4/1999 | Lilley et al. |
| 5,891,086 A | 4/1999 | Weston |
| 5,919,159 A | 7/1999 | Lilley et al. |
| 5,935,949 A | 8/1999 | White |
| 6,045,534 A | 4/2000 | Jacobson et al. |
| 6,077,247 A | 6/2000 | Marshall et al. |
| 6,090,070 A | 7/2000 | Hager et al. |
| 6,099,504 A | 8/2000 | Gross et al. |
| 6,102,896 A | 8/2000 | Roser |
| 6,203,529 B1 | 3/2001 | Gabriel et al. |
| 6,210,369 B1 | 4/2001 | Wilmot et al. |
| 6,221,046 B1 | 4/2001 | Burroughs et al. |
| 6,241,709 B1 | 6/2001 | Bechtold et al. |
| 6,245,347 B1 | 6/2001 | Zhang et al. |
| 6,270,479 B1 | 8/2001 | Bergens et al. |
| 6,371,939 B2 | 4/2002 | Bergens et al. |
| 6,391,003 B1 | 5/2002 | Lesch, Jr. |
| 6,428,528 B2 | 8/2002 | Sadowski et al. |
| 6,517,517 B1 | 2/2003 | Farrugia et al. |
| 6,530,904 B1 | 3/2003 | Edwards et al. |
| 6,544,234 B1 | 4/2003 | Gabriel |
| 6,565,553 B2 | 5/2003 | Sadowski et al. |
| 6,569,123 B2 | 5/2003 | Alchas et al. |
| 6,569,143 B2 | 5/2003 | Alchas et al. |
| 6,607,508 B2 | 8/2003 | Knauer |
| 6,641,561 B1 | 11/2003 | Hill et al. |
| 6,656,150 B2 | 12/2003 | Hill et al. |
| 6,673,035 B1 | 1/2004 | Rice et al. |
| 6,682,504 B2 | 1/2004 | Nelson et al. |
| 6,746,429 B2 | 6/2004 | Sadowski et al. |
| 6,767,336 B1 | 7/2004 | Kaplan |
| 6,830,560 B1 | 12/2004 | Gross et al. |
| 6,932,793 B1 | 8/2005 | Marshall et al. |
| 6,932,794 B2 | 8/2005 | Giambattista et al. |
| 6,969,370 B2 | 11/2005 | Langley et al. |
| 6,969,372 B1 | 11/2005 | Halseth |
| 6,979,316 B1 | 12/2005 | Rubin et al. |
| 6,986,758 B2 | 1/2006 | Schiffmann |
| 6,997,901 B2 | 2/2006 | Popovsky |
| 7,066,907 B2 | 6/2006 | Crossman et al. |
| 7,118,553 B2 | 10/2006 | Scherer |
| 7,169,132 B2 | 1/2007 | Bendek et al. |
| 7,195,616 B2 | 3/2007 | Diller et al. |
| 7,218,962 B2 | 5/2007 | Freyman |
| 7,247,149 B2 | 7/2007 | Beyerlein |
| 7,291,132 B2 | 11/2007 | DeRuntz et al. |
| 7,292,885 B2 | 11/2007 | Scott et al. |
| 7,297,136 B2 | 11/2007 | Wyrick |
| 7,341,575 B2 | 3/2008 | Rice et al. |
| 7,361,160 B2 | 4/2008 | Hommann et al. |
| 7,390,314 B2 | 6/2008 | Stutz, Jr. et al. |
| 7,390,319 B2 | 6/2008 | Friedman |
| 7,407,492 B2 | 8/2008 | Gurtner |
| 7,416,540 B2 | 8/2008 | Edwards et al. |
| 7,449,012 B2 | 11/2008 | Young et al. |
| 7,488,308 B2 | 2/2009 | Lesch, Jr. |
| 7,488,313 B2 | 2/2009 | Segal et al. |
| 7,488,314 B2 | 2/2009 | Segal et al. |
| 7,517,342 B2 | 4/2009 | Scott et al. |
| 7,519,418 B2 | 4/2009 | Scott et al. |
| 7,544,188 B2 | 6/2009 | Edwards et al. |
| 7,547,293 B2 | 6/2009 | Williamson et al. |
| 7,569,035 B1 | 8/2009 | Wilmot et al. |
| 7,611,491 B2 | 11/2009 | Pickhard |
| 7,621,887 B2 | 11/2009 | Griffiths et al. |
| 7,621,891 B2 | 11/2009 | Wyrick |
| 7,635,348 B2 | 12/2009 | Raven et al. |
| 7,637,891 B2 | 12/2009 | Wall |
| 7,648,482 B2 | 1/2010 | Edwards et al. |
| 7,648,483 B2 | 1/2010 | Edwards et al. |
| 7,654,983 B2 | 2/2010 | De La Sema et al. |
| 7,658,724 B2 | 2/2010 | Rubin et al. |
| 7,670,314 B2 | 3/2010 | Wall et al. |
| 7,704,237 B2 | 4/2010 | Fisher et al. |
| 7,717,877 B2 | 5/2010 | Lavi et al. |
| 7,722,595 B2 | 5/2010 | Pettis et al. |
| 7,731,686 B2 | 6/2010 | Edwards et al. |
| 7,731,690 B2 | 6/2010 | Edwards et al. |
| 7,736,333 B2 | 6/2010 | Gillespie, III |
| 7,744,582 B2 | 6/2010 | Sadowski et al. |
| 7,749,194 B2 | 7/2010 | Edwards et al. |
| 7,749,195 B2 | 7/2010 | Hommann |
| 7,762,996 B2 | 7/2010 | Palasis |
| 7,776,015 B2 | 8/2010 | Sadowski et al. |
| 7,794,432 B2 | 9/2010 | Young et al. |
| 7,811,254 B2 | 10/2010 | Wilmot et al. |
| 7,862,543 B2 | 1/2011 | Potter et al. |
| 7,896,841 B2 | 3/2011 | Wall et al. |
| 7,901,377 B1 | 3/2011 | Harrison et al. |
| 7,905,352 B2 | 3/2011 | Wyrick |
| 7,905,866 B2 | 3/2011 | Haider et al. |
| 7,918,823 B2 | 4/2011 | Edwards et al. |
| 7,927,303 B2 | 4/2011 | Wyrick |

(56) References Cited

U.S. PATENT DOCUMENTS

| | | |
|---|---|---|
| 7,931,618 B2 | 4/2011 | Wyrick |
| 7,947,017 B2 | 5/2011 | Edwards et al. |
| RE42,463 E | 6/2011 | Landau |
| 7,955,304 B2 | 6/2011 | Guillermo |
| 7,967,772 B2 | 6/2011 | Mckenzie et al. |
| 7,988,675 B2 | 8/2011 | Gillespie, III et al. |
| 8,016,774 B2 | 9/2011 | Freeman et al. |
| 8,016,788 B2 | 9/2011 | Edwards et al. |
| 8,021,335 B2 | 9/2011 | Lesch, Jr. |
| 8,048,035 B2 | 11/2011 | Mesa et al. |
| 8,048,037 B2 | 11/2011 | Kohlbrenner et al. |
| 8,057,427 B2 | 11/2011 | Griffiths et al. |
| 8,066,659 B2 | 11/2011 | Joshi et al. |
| 8,083,711 B2 | 12/2011 | Enggaard |
| 8,100,865 B2 | 1/2012 | Spofforth |
| 8,105,272 B2 | 1/2012 | Williamson et al. |
| 8,105,281 B2 | 1/2012 | Edwards et al. |
| 8,110,209 B2 | 2/2012 | Prestrelski et al. |
| 8,123,719 B2 | 2/2012 | Edwards et al. |
| 8,123,724 B2 | 2/2012 | Gillespie, III |
| 8,162,873 B2 | 4/2012 | Muto et al. |
| 8,162,886 B2 | 4/2012 | Sadowski et al. |
| 8,167,840 B2 | 5/2012 | Matusch |
| 8,167,866 B2 | 5/2012 | Klein |
| 8,177,758 B2 | 5/2012 | Brooks, Jr. et al. |
| 8,187,224 B2 | 5/2012 | Wyrick |
| 8,216,180 B2 | 7/2012 | Tschirren et al. |
| 8,216,192 B2 | 7/2012 | Burroughs et al. |
| 8,226,618 B2 | 7/2012 | Geertsen |
| 8,226,631 B2 | 7/2012 | Boyd et al. |
| 8,233,135 B2 | 7/2012 | Jansen et al. |
| 8,235,952 B2 | 8/2012 | Wikner |
| 8,246,577 B2 | 8/2012 | Schrul et al. |
| 8,251,947 B2 | 8/2012 | Kramer et al. |
| 8,257,318 B2 | 9/2012 | Thogersen et al. |
| 8,257,319 B2 | 9/2012 | Plumptre |
| 8,267,899 B2 | 9/2012 | Moller |
| 8,267,900 B2 | 9/2012 | Harms et al. |
| 8,273,798 B2 | 9/2012 | Bausch et al. |
| 8,275,454 B2 | 9/2012 | Adachi et al. |
| 8,276,583 B2 | 10/2012 | Farieta et al. |
| 8,277,412 B2 | 10/2012 | Kronestedt |
| 8,277,413 B2 | 10/2012 | Kirchhofer |
| 8,298,175 B2 | 10/2012 | Hirschel et al. |
| 8,298,194 B2 | 10/2012 | Moller |
| 8,300,852 B2 | 10/2012 | Terada |
| RE43,834 E | 11/2012 | Steenfeldt-Jensen et al. |
| 8,308,232 B2 | 11/2012 | Zamperla et al. |
| 8,308,695 B2 | 11/2012 | Laiosa |
| 8,313,466 B2 | 11/2012 | Edwards et al. |
| 8,317,757 B2 | 11/2012 | Plumptre |
| 8,323,237 B2 | 12/2012 | Radmer et al. |
| 8,333,739 B2 | 12/2012 | Moller |
| 8,337,472 B2 | 12/2012 | Edginton et al. |
| 8,343,103 B2 | 1/2013 | Moser |
| 8,343,109 B2 | 1/2013 | Marshall et al. |
| 8,348,905 B2 | 1/2013 | Radmer et al. |
| 8,353,878 B2 | 1/2013 | Moller et al. |
| 8,357,120 B2 | 1/2013 | Moller et al. |
| 8,357,125 B2 | 1/2013 | Grunhut et al. |
| 8,361,036 B2 | 1/2013 | Moller et al. |
| 8,366,680 B2 | 2/2013 | Raab |
| 8,372,031 B2 | 2/2013 | Elmen et al. |
| 8,372,042 B2 | 2/2013 | Wieselblad |
| 8,376,993 B2 | 2/2013 | Cox et al. |
| 8,398,593 B2 | 3/2013 | Fich et al. |
| 8,409,149 B2 | 4/2013 | Hommann et al. |
| 8,435,215 B2 | 5/2013 | Arby et al. |
| 2001/0039394 A1 | 11/2001 | Weston |
| 2002/0173752 A1 | 11/2002 | Polzin |
| 2003/0040697 A1 | 2/2003 | Pass et al. |
| 2003/0171717 A1 | 9/2003 | Farrugia et al. |
| 2004/0039337 A1 | 2/2004 | Etzing |
| 2004/0143213 A1 | 7/2004 | Hunter et al. |
| 2004/0220524 A1 | 11/2004 | Sadowski et al. |
| 2004/0267355 A1 | 12/2004 | Scott et al. |
| 2005/0027255 A1 | 2/2005 | Lavi et al. |
| 2005/0101919 A1 | 5/2005 | Brunnberg |
| 2005/0165363 A1 | 7/2005 | Judson et al. |
| 2005/0209569 A1 | 9/2005 | Ishikawa et al. |
| 2005/0215955 A1 | 9/2005 | Slawson |
| 2005/0240145 A1 | 10/2005 | Scott et al. |
| 2005/0256499 A1 | 11/2005 | Pettis et al. |
| 2005/0273054 A1 | 12/2005 | Asch |
| 2006/0106362 A1 | 5/2006 | Pass et al. |
| 2006/0129122 A1 | 6/2006 | Wyrick |
| 2006/0224124 A1 | 10/2006 | Scherer |
| 2006/0258988 A1 | 11/2006 | Keitel et al. |
| 2006/0258990 A1 | 11/2006 | Weber |
| 2007/0017533 A1 | 1/2007 | Wyrick |
| 2007/0025890 A1 | 2/2007 | Joshi et al. |
| 2007/0027430 A1 | 2/2007 | Hommann |
| 2007/0100288 A1 | 5/2007 | Bozeman et al. |
| 2007/0112310 A1 | 5/2007 | Lavi et al. |
| 2007/0123818 A1 | 5/2007 | Griffiths et al. |
| 2007/0129687 A1 | 6/2007 | Marshall et al. |
| 2007/0185432 A1 | 8/2007 | Etheredge et al. |
| 2007/0191784 A1 | 8/2007 | Jacobs et al. |
| 2007/0219498 A1 | 9/2007 | Malone et al. |
| 2008/0059133 A1 | 3/2008 | Edwards et al. |
| 2008/0154199 A1 | 6/2008 | Wyrick |
| 2008/0262427 A1 | 10/2008 | Hommann |
| 2008/0262436 A1 | 10/2008 | Olson |
| 2008/0262445 A1 | 10/2008 | Hsu et al. |
| 2009/0124981 A1 | 5/2009 | Evans |
| 2009/0124997 A1 | 5/2009 | Pettis et al. |
| 2009/0204062 A1 | 8/2009 | Muto et al. |
| 2009/0254035 A1 | 10/2009 | Kohlbrenner et al. |
| 2009/0299278 A1 | 12/2009 | Lesch, Jr. et al. |
| 2009/0304812 A1 | 12/2009 | Stainforth et al. |
| 2009/0318361 A1 | 12/2009 | Noera et al. |
| 2010/0036318 A1 | 2/2010 | Raday et al. |
| 2010/0049125 A1 | 2/2010 | James et al. |
| 2010/0069845 A1 | 3/2010 | Marshall et al. |
| 2010/0076378 A1 | 3/2010 | Runfola |
| 2010/0076400 A1 | 3/2010 | Wall |
| 2010/0087847 A1 | 4/2010 | Hong |
| 2010/0094214 A1 | 4/2010 | Abry et al. |
| 2010/0094324 A1 | 4/2010 | Huang et al. |
| 2010/0100039 A1 | 4/2010 | Wyrick |
| 2010/0152699 A1 | 6/2010 | Ferrari et al. |
| 2010/0152702 A1 | 6/2010 | Vigil et al. |
| 2010/0160894 A1 | 6/2010 | Julian et al. |
| 2010/0168677 A1 | 7/2010 | Gabriel et al. |
| 2010/0174268 A1 | 7/2010 | Wilmot et al. |
| 2010/0204678 A1 | 8/2010 | Imran |
| 2010/0217105 A1 | 8/2010 | Yodfat et al. |
| 2010/0228193 A1 | 9/2010 | Wyrick |
| 2010/0249746 A1 | 9/2010 | Klein |
| 2010/0256570 A1 | 10/2010 | Maritan |
| 2010/0258631 A1 | 10/2010 | Rueblinger et al. |
| 2010/0262082 A1 | 10/2010 | Brooks et al. |
| 2010/0274198 A1 | 10/2010 | Bechtold |
| 2010/0274273 A1 | 10/2010 | Schraga et al. |
| 2010/0288593 A1 | 11/2010 | Chiesa et al. |
| 2010/0292643 A1 | 11/2010 | Wilmot et al. |
| 2010/0298780 A1 | 11/2010 | Laiosa |
| 2010/0312196 A1 | 12/2010 | Hirschel et al. |
| 2010/0318035 A1 | 12/2010 | Edwards et al. |
| 2010/0318037 A1 | 12/2010 | Young et al. |
| 2010/0324480 A1 | 12/2010 | Chun |
| 2011/0021989 A1 | 1/2011 | Janek et al. |
| 2011/0054414 A1 | 3/2011 | Shang et al. |
| 2011/0077599 A1 | 3/2011 | Wozencroft |
| 2011/0087192 A1 | 4/2011 | Uhland et al. |
| 2011/0098655 A1 | 4/2011 | Jennings et al. |
| 2011/0125076 A1 | 5/2011 | Kraft et al. |
| 2011/0125100 A1 | 5/2011 | Schwirtz et al. |
| 2011/0137246 A1 | 6/2011 | Cali et al. |
| 2011/0144594 A1* | 6/2011 | Sund ............... A61M 5/31571<br>604/228 |
| 2011/0190725 A1 | 8/2011 | Pettis et al. |
| 2011/0196300 A1 | 8/2011 | Edwards et al. |
| 2011/0196311 A1 | 8/2011 | Bicknell et al. |

(56) References Cited

U.S. PATENT DOCUMENTS

| | | |
|---|---|---|
| 2011/0208119 A1 | 8/2011 | Asmussen et al. |
| 2011/0224620 A1 | 9/2011 | Johansen et al. |
| 2011/0238003 A1 | 9/2011 | Bruno-Raimondi et al. |
| 2011/0269750 A1 | 11/2011 | Kley et al. |
| 2011/0319864 A1 | 12/2011 | Beller et al. |
| 2012/0004608 A1* | 1/2012 | Lesch, Jr. .............. A61M 5/178 604/135 |
| 2012/0016296 A1 | 1/2012 | Cleathero |
| 2012/0046609 A1 | 2/2012 | Mesa et al. |
| 2012/0053563 A1 | 3/2012 | Du |
| 2012/0059319 A1 | 3/2012 | Segal |
| 2012/0071829 A1 | 3/2012 | Edwards et al. |
| 2012/0095443 A1 | 4/2012 | Ferrari et al. |
| 2012/0101475 A1 | 4/2012 | Wilmot et al. |
| 2012/0116318 A1 | 5/2012 | Edwards et al. |
| 2012/0123350 A1 | 5/2012 | Giambattista et al. |
| 2012/0123385 A1 | 5/2012 | Edwards et al. |
| 2012/0130318 A1 | 5/2012 | Young |
| 2012/0130342 A1 | 5/2012 | Cleathero |
| 2012/0136303 A1 | 5/2012 | Cleathero |
| 2012/0136318 A1 | 5/2012 | Anin et al. |
| 2012/0143144 A1 | 6/2012 | Young |
| 2012/0157931 A1 | 6/2012 | Nzike |
| 2012/0157965 A1 | 6/2012 | Wotton et al. |
| 2012/0172809 A1 | 7/2012 | Plumptre |
| 2012/0172811 A1 | 7/2012 | Enggaard et al. |
| 2012/0172812 A1 | 7/2012 | Plumptre et al. |
| 2012/0172813 A1 | 7/2012 | Plumptre et al. |
| 2012/0172814 A1 | 7/2012 | Plumptre et al. |
| 2012/0172815 A1 | 7/2012 | Holmqvist |
| 2012/0172816 A1 | 7/2012 | Boyd et al. |
| 2012/0172818 A1 | 7/2012 | Harms et al. |
| 2012/0179100 A1 | 7/2012 | Sadowski et al. |
| 2012/0179137 A1 | 7/2012 | Bartlett et al. |
| 2012/0184900 A1 | 7/2012 | Marshall et al. |
| 2012/0184917 A1 | 7/2012 | Bom et al. |
| 2012/0184918 A1 | 7/2012 | Bostrom |
| 2012/0186075 A1 | 7/2012 | Edginton |
| 2012/0191048 A1 | 7/2012 | Eaton |
| 2012/0191049 A1 | 7/2012 | Harms et al. |
| 2012/0197209 A1 | 8/2012 | Bicknell et al. |
| 2012/0197213 A1 | 8/2012 | Kohlbrenner et al. |
| 2012/0203184 A1 | 8/2012 | Selz et al. |
| 2012/0203185 A1 | 8/2012 | Kristensen et al. |
| 2012/0203186 A1 | 8/2012 | Vogt et al. |
| 2012/0209192 A1 | 8/2012 | Alexandersson |
| 2012/0209200 A1 | 8/2012 | Jones et al. |
| 2012/0209210 A1 | 8/2012 | Plumptre et al. |
| 2012/0209211 A1 | 8/2012 | Plumptre et al. |
| 2012/0209212 A1 | 8/2012 | Plumptre et al. |
| 2012/0215162 A1 | 8/2012 | Nielsen et al. |
| 2012/0215176 A1 | 8/2012 | Veasey et al. |
| 2012/0220929 A1 | 8/2012 | Nagel et al. |
| 2012/0220941 A1 | 8/2012 | Jones |
| 2012/0220953 A1 | 8/2012 | Holmqvist |
| 2012/0220954 A1 | 8/2012 | Cowe |
| 2012/0226226 A1 | 9/2012 | Edwards et al. |
| 2012/0230620 A1 | 9/2012 | Holdgate et al. |
| 2012/0232517 A1 | 9/2012 | Saiki |
| 2012/0245516 A1 | 9/2012 | Tschirren et al. |
| 2012/0245532 A1 | 9/2012 | Frantz et al. |
| 2012/0253274 A1 | 10/2012 | Karlsson et al. |
| 2012/0253287 A1 | 10/2012 | Giambattista et al. |
| 2012/0253288 A1 | 10/2012 | Dasbach et al. |
| 2012/0253289 A1 | 10/2012 | Cleathero |
| 2012/0253290 A1 | 10/2012 | Geertsen |
| 2012/0253314 A1 | 10/2012 | Harish et al. |
| 2012/0259285 A1 | 10/2012 | Schabbach et al. |
| 2012/0265153 A1 | 10/2012 | Jugl et al. |
| 2012/0267761 A1 | 10/2012 | Kim et al. |
| 2012/0271233 A1 | 10/2012 | Bruggemann et al. |
| 2012/0271243 A1 | 10/2012 | Plumptre et al. |
| 2012/0277724 A1 | 11/2012 | Larsen et al. |
| 2012/0283645 A1 | 11/2012 | Veasey et al. |
| 2012/0283648 A1 | 11/2012 | Veasey et al. |
| 2012/0283649 A1 | 11/2012 | Veasey et al. |
| 2012/0283650 A1 | 11/2012 | MacDonald et al. |
| 2012/0283651 A1 | 11/2012 | Veasey et al. |
| 2012/0283652 A1 | 11/2012 | MacDonald et al. |
| 2012/0283654 A1 | 11/2012 | MacDonald et al. |
| 2012/0283660 A1 | 11/2012 | Jones et al. |
| 2012/0283661 A1 | 11/2012 | Jugl et al. |
| 2012/0289907 A1 | 11/2012 | Veasey et al. |
| 2012/0289908 A1 | 11/2012 | Kouyoumjian et al. |
| 2012/0289909 A1 | 11/2012 | Raab et al. |
| 2012/0289929 A1 | 11/2012 | Boyd et al. |
| 2012/0291778 A1 | 11/2012 | Nagel et al. |
| 2012/0296276 A1 | 11/2012 | Nicholls et al. |
| 2012/0296287 A1 | 11/2012 | Veasey et al. |
| 2012/0302989 A1 | 11/2012 | Kramer et al. |
| 2012/0302992 A1 | 11/2012 | Brooks et al. |
| 2012/0310156 A1 | 12/2012 | Karlsson et al. |
| 2012/0310206 A1 | 12/2012 | Kouyoumjian et al. |
| 2012/0310208 A1 | 12/2012 | Kirchhofer |
| 2012/0310289 A1 | 12/2012 | Bottlang et al. |
| 2012/0316508 A1 | 12/2012 | Kirchhofer |
| 2012/0323177 A1 | 12/2012 | Adams et al. |
| 2012/0323186 A1 | 12/2012 | Karlsen et al. |
| 2012/0325865 A1 | 12/2012 | Forstreuter et al. |
| 2012/0330228 A1 | 12/2012 | Day et al. |
| 2013/0006191 A1 | 1/2013 | Jugl et al. |
| 2013/0006192 A1 | 1/2013 | Teucher et al. |
| 2013/0006193 A1 | 1/2013 | Veasey et al. |
| 2013/0006310 A1 | 1/2013 | Bottlang et al. |
| 2013/0012871 A1 | 1/2013 | Pommereu |
| 2013/0012884 A1 | 1/2013 | Pommerau et al. |
| 2013/0012885 A1 | 1/2013 | Bode et al. |
| 2013/0018310 A1 | 1/2013 | Boyd et al. |
| 2013/0018313 A1 | 1/2013 | Kramer et al. |
| 2013/0018317 A1 | 1/2013 | Bobroff et al. |
| 2013/0018323 A1 | 1/2013 | Boyd et al. |
| 2013/0018327 A1 | 1/2013 | Dasbach et al. |
| 2013/0018328 A1 | 1/2013 | Jugl et al. |
| 2013/0023830 A1 | 1/2013 | Bode |
| 2013/0030367 A1 | 1/2013 | Wotton et al. |
| 2013/0030378 A1 | 1/2013 | Jugl et al. |
| 2013/0030383 A1 | 1/2013 | Keitel |
| 2013/0030409 A1 | 1/2013 | Macdonald et al. |
| 2013/0035641 A1 | 2/2013 | Moller et al. |
| 2013/0035642 A1 | 2/2013 | Daniel |
| 2013/0035644 A1 | 2/2013 | Giambattista et al. |
| 2013/0035645 A1 | 2/2013 | Bicknell et al. |
| 2013/0035647 A1 | 2/2013 | Veasey et al. |
| 2013/0041321 A1 | 2/2013 | Cross et al. |
| 2013/0041324 A1 | 2/2013 | Daniel |
| 2013/0041325 A1 | 2/2013 | Helmer et al. |
| 2013/0041327 A1 | 2/2013 | Daniel |
| 2013/0041328 A1 | 2/2013 | Daniel |
| 2013/0041347 A1 | 2/2013 | Daniel |
| 2013/0060231 A1 | 3/2013 | Adlon et al. |

FOREIGN PATENT DOCUMENTS

| | | |
|---|---|---|
| AU | 2007253481 | 11/2007 |
| AU | 2007301890 | 4/2008 |
| AU | 2008231897 | 10/2008 |
| AU | 2008309660 | 4/2009 |
| AU | 2009217376 | 10/2009 |
| AU | 2009272992 | 1/2010 |
| AU | 2009299888 | 4/2010 |
| AU | 2009326132 | 8/2011 |
| AU | 2009326321 | 8/2011 |
| AU | 2009326322 | 8/2011 |
| AU | 2009326323 | 8/2011 |
| AU | 2009326324 | 8/2011 |
| AU | 2009326325 | 8/2011 |
| AU | 2009341040 | 9/2011 |
| AU | 2010233924 | 11/2011 |
| AU | 2010239762 | 12/2011 |
| AU | 2010242096 | 12/2011 |
| AU | 2010254627 | 1/2012 |
| AU | 2010260568 | 2/2012 |
| AU | 2010260569 | 2/2012 |
| AU | 2010287033 | 4/2012 |

(56) References Cited

FOREIGN PATENT DOCUMENTS

| | | |
|---|---|---|
| AU | 2010303987 | 5/2012 |
| AU | 2010332857 | 7/2012 |
| AU | 2010332862 | 7/2012 |
| AU | 2010337136 | 7/2012 |
| AU | 2010338469 | 7/2012 |
| AU | 2010314315 | 8/2012 |
| AU | 2011212490 | 8/2012 |
| AU | 2011212556 | 8/2012 |
| AU | 2011212558 | 8/2012 |
| AU | 2011212561 | 8/2012 |
| AU | 2011212564 | 8/2012 |
| AU | 2011212566 | 8/2012 |
| AU | 2011212567 | 8/2012 |
| AU | 2011214922 | 8/2012 |
| AU | 2011221472 | 8/2012 |
| AU | 2011231688 | 9/2012 |
| AU | 2011231691 | 9/2012 |
| AU | 2011224884 | 10/2012 |
| AU | 2011231570 | 10/2012 |
| AU | 2011231697 | 10/2012 |
| AU | 2011233733 | 10/2012 |
| AU | 2011234479 | 10/2012 |
| AU | 2011238967 | 11/2012 |
| AU | 2011244232 | 11/2012 |
| AU | 2011244236 | 11/2012 |
| AU | 2011244237 | 11/2012 |
| AU | 2011249098 | 11/2012 |
| AU | 2011262408 | 12/2012 |
| AU | 2011270934 | 1/2013 |
| AU | 2011273721 | 1/2013 |
| AU | 2011273722 | 1/2013 |
| AU | 2011273723 | 1/2013 |
| AU | 2011273724 | 1/2013 |
| AU | 2011273725 | 1/2013 |
| AU | 2011273726 | 1/2013 |
| AU | 2011273727 | 1/2013 |
| AU | 2011273728 | 1/2013 |
| BR | 0208013 | 3/2004 |
| BR | 0308262 | 1/2005 |
| BR | PI712805 | 10/2012 |
| BR | PI0713802-4 | 11/2012 |
| BR | 0214721 | 12/2012 |
| CA | 2552177 | 7/1999 |
| CA | 2689022 | 11/2002 |
| CA | 2473371 | 7/2003 |
| CA | 2557897 | 10/2005 |
| CA | 02702412 | 12/2008 |
| CN | 101094700 | 12/2007 |
| CN | 101128231 | 2/2008 |
| CN | 101184520 | 5/2008 |
| CN | 101400394 | 4/2009 |
| CN | 101405582 | 4/2009 |
| CN | 101479000 | 7/2009 |
| CN | 101511410 | 8/2009 |
| CN | 101516421 | 8/2009 |
| CN | 101557849 | 10/2009 |
| CN | 101563123 | 10/2009 |
| CN | 101563124 | 10/2009 |
| CN | 101594898 | 12/2009 |
| CN | 101600468 | 12/2009 |
| CN | 101605569 | 12/2009 |
| CN | 101610804 | 12/2009 |
| CN | 101626796 | 1/2010 |
| CN | 101678166 | 3/2010 |
| CN | 101678172 | 3/2010 |
| CN | 101678173 | 3/2010 |
| CN | 101687078 | 3/2010 |
| CN | 101687079 | 3/2010 |
| CN | 101687080 | 3/2010 |
| CN | 101715371 | 5/2010 |
| CN | 101909673 | 12/2010 |
| CN | 101912650 | 12/2010 |
| CN | 101939034 | 1/2011 |
| CN | 101939036 | 1/2011 |
| CN | 102548599 | 7/2012 |
| CN | 102548601 | 7/2012 |
| CN | 102548602 | 7/2012 |
| CN | 102573955 | 7/2012 |
| CN | 102573958 | 7/2012 |
| CN | 102573960 | 7/2012 |
| CN | 102573963 | 7/2012 |
| CN | 102630172 | 8/2012 |
| CN | 102630173 | 8/2012 |
| CN | 102630174 | 8/2012 |
| CN | 102639170 | 8/2012 |
| CN | 102639171 | 8/2012 |
| CN | 102648014 | 8/2012 |
| CN | 102655899 | 9/2012 |
| CN | 102665800 | 9/2012 |
| CN | 102665802 | 9/2012 |
| CN | 102686255 | 9/2012 |
| CN | 102686256 | 9/2012 |
| CN | 102686258 | 9/2012 |
| CN | 102695531 | 9/2012 |
| CN | 102695532 | 9/2012 |
| CN | 102711878 | 10/2012 |
| CN | 102727965 | 10/2012 |
| CN | 102740907 | 10/2012 |
| CN | 102753222 | 10/2012 |
| CN | 102753223 | 10/2012 |
| CN | 102753224 | 10/2012 |
| CN | 102753227 | 10/2012 |
| CN | 102770170 | 11/2012 |
| CN | 102770173 | 11/2012 |
| CN | 102781499 | 11/2012 |
| CN | 102781500 | 11/2012 |
| CN | 102802699 | 11/2012 |
| CN | 102802702 | 11/2012 |
| CN | 102802703 | 11/2012 |
| CN | 102665801 | 12/2012 |
| CN | 102821801 | 12/2012 |
| CN | 102821802 | 12/2012 |
| CN | 102821805 | 12/2012 |
| CN | 102834133 | 12/2012 |
| CN | 102869399 | 1/2013 |
| CN | 102895718 | 1/2013 |
| CN | 102905613 | 1/2013 |
| CN | 102905742 | 1/2013 |
| CN | 102905743 | 1/2013 |
| CN | 102905744 | 1/2013 |
| CN | 102905745 | 1/2013 |
| CN | 102917738 | 2/2013 |
| CN | 102917743 | 2/2013 |
| DE | 102006041809 | 3/2008 |
| DE | 202011110155 | 12/2012 |
| DK | 1646844 | 12/2009 |
| DK | 2229201 | 7/2012 |
| DK | 2023982 | 10/2012 |
| DK | 2274032 | 10/2012 |
| DK | 02346552 | 11/2012 |
| DK | 1888148 | 1/2013 |
| DK | 2288400 | 1/2013 |
| DK | 2373361 | 1/2013 |
| DK | 1885414 | 2/2013 |
| DK | 2174682 | 2/2013 |
| DK | 2310073 | 2/2013 |
| EG | 25844 | 9/2012 |
| EP | 245895 | 11/1987 |
| EP | 255044 | 2/1988 |
| EP | 361668 | 4/1990 |
| EP | 525525 | 2/1993 |
| EP | 1067823 | 1/2001 |
| EP | 1307012 | 5/2003 |
| EP | 1140260 | 8/2005 |
| EP | 1944050 | 7/2008 |
| EP | 2174682 | 4/2010 |
| EP | 2258424 | 12/2010 |
| EP | 2258425 | 12/2010 |
| EP | 02275158 | 1/2011 |
| EP | 2364742 | 9/2011 |
| EP | 2393062 | 12/2011 |
| EP | 2471564 | 7/2012 |
| EP | 02477681 | 7/2012 |
| EP | 02484395 | 8/2012 |

(56) References Cited

FOREIGN PATENT DOCUMENTS

| | | |
|---|---|---|
| EP | 2526987 | 11/2012 |
| EP | 02529773 | 12/2012 |
| EP | 02529774 | 12/2012 |
| EP | 02529775 | 12/2012 |
| EP | 2549789 | 1/2013 |
| EP | 2900299 B1 | 7/2020 |
| ES | 02385630 | 7/2012 |
| ES | 2389866 | 11/2012 |
| ES | 2392667 | 12/2012 |
| ES | 02393173 | 12/2012 |
| ES | 2394556 | 2/2013 |
| GB | 2463034 | 3/2010 |
| IL | 171247 | 8/2012 |
| IL | 198750 | 10/2012 |
| JP | H 8-505543 A | 6/1998 |
| JP | 2003-512904 A | 4/2003 |
| JP | 2007-500530 A | 1/2007 |
| JP | 5016490 | 5/2008 |
| JP | 2008-528126 A | 7/2008 |
| JP | 5026411 | 11/2008 |
| JP | 5033792 | 11/2008 |
| JP | 5074397 | 2/2009 |
| JP | 2009-529395 | 8/2009 |
| JP | 5066177 | 9/2009 |
| JP | 5039135 | 11/2009 |
| JP | 5044625 | 12/2009 |
| JP | 2010-005414 | 1/2010 |
| JP | 2010-046507 | 3/2010 |
| JP | 2011-513035 A | 4/2011 |
| JP | 4970282 | 7/2012 |
| JP | 4970286 | 7/2012 |
| JP | 4972147 | 7/2012 |
| JP | 4977209 | 7/2012 |
| JP | 4977252 | 7/2012 |
| JP | 4979686 | 7/2012 |
| JP | 4982722 | 7/2012 |
| JP | 2012515566 | 7/2012 |
| JP | 2012515585 | 7/2012 |
| JP | 2012515587 | 7/2012 |
| JP | 2012516168 | 7/2012 |
| JP | 2012516736 | 7/2012 |
| JP | 2012516737 | 7/2012 |
| JP | 4990151 | 8/2012 |
| JP | 4992147 | 8/2012 |
| JP | 4994370 | 8/2012 |
| JP | 5001001 | 8/2012 |
| JP | 2012143646 | 8/2012 |
| JP | 2012148198 | 8/2012 |
| JP | 2012519508 | 8/2012 |
| JP | 2012519514 | 8/2012 |
| JP | UP 2012519511 | 8/2012 |
| JP | 2012176295 | 9/2012 |
| JP | 2012183322 | 9/2012 |
| JP | 2012520128 | 9/2012 |
| JP | 2012521821 | 9/2012 |
| JP | 2012521825 | 9/2012 |
| JP | 2012521826 | 9/2012 |
| JP | 2012521827 | 9/2012 |
| JP | 2012521828 | 9/2012 |
| JP | 2012521829 | 9/2012 |
| JP | 2012521830 | 9/2012 |
| JP | 2012521831 | 9/2012 |
| JP | 2012521834 | 9/2012 |
| JP | 2012522547 | 9/2012 |
| JP | 2012-525172 | 10/2012 |
| JP | 2012-525180 | 10/2012 |
| JP | 2012-525185 | 10/2012 |
| JP | 2012523876 | 10/2012 |
| JP | 2012525200 | 10/2012 |
| JP | 5084825 | 11/2012 |
| JP | 2012232151 | 11/2012 |
| JP | 2012528618 | 11/2012 |
| JP | 2012528619 | 11/2012 |
| JP | 2012528620 | 11/2012 |
| JP | 2012528621 | 11/2012 |
| JP | 2012528622 | 11/2012 |
| JP | 2012528623 | 11/2012 |
| JP | 2012528624 | 11/2012 |
| JP | 2012528625 | 11/2012 |
| JP | 2012528626 | 11/2012 |
| JP | 2012528627 | 11/2012 |
| JP | 2012528628 | 11/2012 |
| JP | 2012528629 | 11/2012 |
| JP | 2012528630 | 11/2012 |
| JP | 2012528631 | 11/2012 |
| JP | 2012528632 | 11/2012 |
| JP | 2012528633 | 11/2012 |
| JP | 2012528634 | 11/2012 |
| JP | 2012528635 | 11/2012 |
| JP | 2012528636 | 11/2012 |
| JP | 2012528637 | 11/2012 |
| JP | 2012528638 | 11/2012 |
| JP | 2012528640 | 11/2012 |
| JP | 2012530576 | 12/2012 |
| JP | 2012532635 | 12/2012 |
| JP | 2012532636 | 12/2012 |
| JP | 2012532717 | 12/2012 |
| JP | 2012532720 | 12/2012 |
| JP | 2012532721 | 12/2012 |
| JP | 2012532722 | 12/2012 |
| JP | 5112330 | 1/2013 |
| JP | 5113847 | 1/2013 |
| JP | 2015-521055 A | 7/2015 |
| KR | 101160735 | 7/2012 |
| KR | 20120091009 | 8/2012 |
| KR | 20120091153 | 8/2012 |
| KR | 20120091154 | 8/2012 |
| KR | 20120095919 | 8/2012 |
| KR | 20120099022 | 9/2012 |
| KR | 20120099101 | 9/2012 |
| KR | 20120102597 | 9/2012 |
| KR | 20120106754 | 9/2012 |
| KR | 20120106756 | 9/2012 |
| KR | 20120112503 | 10/2012 |
| MX | 2012006694 | 7/2012 |
| NO | 332622 | 10/2003 |
| NZ | 572765 | 8/2012 |
| NZ | 587235 | 8/2012 |
| NZ | 00590352 | 10/2012 |
| PL | 2023982 | 11/2012 |
| PT | 2274032 | 10/2012 |
| PT | 2346552 | 11/2012 |
| RU | 2462275 | 3/2011 |
| RU | 2459247 | 8/2012 |
| RU | 2011104496 | 8/2012 |
| RU | 2460546 | 9/2012 |
| RU | 2011109925 | 10/2012 |
| RU | 2011119019 | 11/2012 |
| SG | 181710 | 7/2012 |
| SG | 181790 | 7/2012 |
| SG | 184182 | 10/2012 |
| SG | 184328 | 11/2012 |
| SG | 184500 | 11/2012 |
| SG | 184501 | 11/2012 |
| SG | 184502 | 11/2012 |
| SI | 2274032 | 12/2012 |
| SI | 2346552 | 12/2012 |
| WO | WO 88/08724 | 11/1988 |
| WO | WO 91/13299 | 9/1991 |
| WO | WO 91/13430 | 9/1991 |
| WO | 9411041 A1 | 5/1994 |
| WO | WO 94/11041 | 5/1994 |
| WO | WO 1994011041 A1 | 5/1994 |
| WO | WO 9831369 | 7/1998 |
| WO | WO 9832451 | 7/1998 |
| WO | WO 9922789 | 5/1999 |
| WO | WO 9962525 | 12/1999 |
| WO | WO 0006228 | 2/2000 |
| WO | 01/32255 A1 | 5/2001 |
| WO | WO 02/083216 | 10/2002 |
| WO | WO 2089805 | 11/2002 |
| WO | WO 3047663 | 6/2003 |
| WO | WO 3068290 | 8/2003 |
| WO | WO 03070296 | 8/2003 |

(56) References Cited

FOREIGN PATENT DOCUMENTS

| | | |
|---|---|---|
| WO | 03095003 A1 | 11/2003 |
| WO | WO 3097133 | 11/2003 |
| WO | WO 2003095003 A1 | 11/2003 |
| WO | WO 2004/041331 | 5/2004 |
| WO | WO 2004/047892 | 6/2004 |
| WO | 2004/086631 A2 | 10/2004 |
| WO | WO 2005/005929 | 1/2005 |
| WO | WO 2005/009515 | 2/2005 |
| WO | WO 2005/053778 | 6/2005 |
| WO | 2006/079064 A1 | 7/2006 |
| WO | WO 2006/125328 | 11/2006 |
| WO | WO 2006/130098 | 12/2006 |
| WO | WO 2007/063342 | 6/2007 |
| WO | WO 2007/100899 | 9/2007 |
| WO | WO 2006/079064 | 11/2007 |
| WO | WO 2007/129106 | 11/2007 |
| WO | WO 2007/131013 | 11/2007 |
| WO | WO 2007/131025 | 11/2007 |
| WO | WO 2007/143676 | 12/2007 |
| WO | WO 2008/005315 | 1/2008 |
| WO | WO 2008/009476 | 1/2008 |
| WO | WO 2008/058666 | 5/2008 |
| WO | WO 2008/100576 | 8/2008 |
| WO | WO 2008/107378 | 9/2008 |
| WO | WO 2007/104636 | 12/2008 |
| WO | WO 2009049885 | 4/2009 |
| WO | WO 2008/071804 | 8/2009 |
| WO | 2009/114542 A1 | 9/2009 |
| WO | WO 2009/114542 | 9/2009 |
| WO | WO 2009/132778 | 11/2009 |
| WO | WO 2009/141005 | 11/2009 |
| WO | WO 2010/003569 | 1/2010 |
| WO | WO 2010/043533 | 4/2010 |
| WO | WO 2010/046394 | 4/2010 |
| WO | WO 2010/097116 | 9/2010 |
| WO | WO 2010/108116 | 9/2010 |
| WO | WO 2010136078 A1 | 12/2010 |
| WO | WO 2011/023736 | 3/2011 |
| WO | WO 2011/023882 | 3/2011 |
| WO | WO 2011/035877 | 3/2011 |
| WO | WO 2011/036133 | 3/2011 |
| WO | WO 2011/036134 | 3/2011 |
| WO | WO 2011/039163 | 4/2011 |
| WO | WO 2011/039201 | 4/2011 |
| WO | WO 2011/039202 | 4/2011 |
| WO | WO 2011/039207 | 4/2011 |
| WO | WO 2011/039208 | 4/2011 |
| WO | WO 2011/039209 | 4/2011 |
| WO | WO 2011/039211 | 4/2011 |
| WO | WO 2011/039216 | 4/2011 |
| WO | WO 2011/039217 | 4/2011 |
| WO | WO 2011/039218 | 4/2011 |
| WO | WO 2011/039219 | 4/2011 |
| WO | WO 2011/039228 | 4/2011 |
| WO | WO 2011/039231 | 4/2011 |
| WO | WO 2011/039232 | 4/2011 |
| WO | WO 2011/039233 | 4/2011 |
| WO | WO 2011/039236 | 4/2011 |
| WO | WO 2011/040861 | 4/2011 |
| WO | WO 2011/045385 | 4/2011 |
| WO | WO 2011/045386 | 4/2011 |
| WO | WO 2011/045611 | 4/2011 |
| WO | WO 2011/046756 | 4/2011 |
| WO | WO 2011/048223 | 4/2011 |
| WO | WO 2011/048422 | 4/2011 |
| WO | WO 2011/050359 | 4/2011 |
| WO | WO 2011/053225 | 5/2011 |
| WO | WO 2011/054648 | 5/2011 |
| WO | WO 2011/054775 | 5/2011 |
| WO | WO 2011/056127 | 5/2011 |
| WO | WO 2011/060087 | 5/2011 |
| WO | WO 2011/067187 | 6/2011 |
| WO | WO 2011/067268 | 6/2011 |
| WO | WO 2011/067320 | 6/2011 |
| WO | WO 2011/067615 | 6/2011 |
| WO | WO 2011/068253 | 6/2011 |
| WO | WO 2011/069936 | 6/2011 |
| WO | WO 2011/073302 | 6/2011 |
| WO | WO 2011/073307 | 6/2011 |
| WO | WO 2011/076280 | 6/2011 |
| WO | WO 2011/080092 | 7/2011 |
| WO | WO 2011/081867 | 7/2011 |
| WO | WO 2011/081885 | 7/2011 |
| WO | WO 2011/089206 | 7/2011 |
| WO | WO 2011/089207 | 7/2011 |
| WO | WO 2011/095478 | 8/2011 |
| WO | WO 2011/095480 | 8/2011 |
| WO | WO 2011/095483 | 8/2011 |
| WO | WO 2011/095486 | 8/2011 |
| WO | WO 2011/095488 | 8/2011 |
| WO | WO 2011/095489 | 8/2011 |
| WO | WO 2011/095503 | 8/2011 |
| WO | WO 2011/099918 | 8/2011 |
| WO | WO 2011/101349 | 8/2011 |
| WO | WO 2011/101351 | 8/2011 |
| WO | WO 2011/101375 | 8/2011 |
| WO | WO 2011/101376 | 8/2011 |
| WO | WO 2011/101377 | 8/2011 |
| WO | WO 2011/101378 | 8/2011 |
| WO | WO 2011/101379 | 8/2011 |
| WO | WO 2011/101380 | 8/2011 |
| WO | WO 2011/101381 | 8/2011 |
| WO | WO 2011/101382 | 8/2011 |
| WO | WO 2011/101383 | 8/2011 |
| WO | 2011/117404 | 9/2011 |
| WO | WO 2011/107805 | 9/2011 |
| WO | WO 2011/109205 | 9/2011 |
| WO | WO 2011/110464 | 9/2011 |
| WO | WO 2011/110465 | 9/2011 |
| WO | WO 2011/110466 | 9/2011 |
| WO | WO 2011/111006 | 9/2011 |
| WO | WO 2011/112136 | 9/2011 |
| WO | WO 2011/113806 | 9/2011 |
| WO | WO 2011/117212 | 9/2011 |
| WO | WO 2011/117284 | 9/2011 |
| WO | WO 2011/121003 | 10/2011 |
| WO | WO 2011/121061 | 10/2011 |
| WO | WO 2011/123024 | 10/2011 |
| WO | WO 2011/124634 | 10/2011 |
| WO | WO 2011/126439 | 10/2011 |
| WO | WO 2012020084 | 2/2012 |
| WO | WO 2012022771 | 2/2012 |
| WO | WO 2012/090186 | 7/2012 |
| WO | WO 2011/042537 | 8/2012 |
| WO | WO 2011/042540 | 8/2012 |
| WO | WO 2011/043714 | 8/2012 |
| WO | WO 2011/051366 | 9/2012 |
| WO | WO 2012/122643 | 9/2012 |
| WO | 2013/134244 A2 | 9/2023 |

OTHER PUBLICATIONS

Office Action for Japanese Patent Application No. 2014-561030 dated Jul. 7, 2016, 11 pages.
English Summary of Office Action for Japanese Patent Application No. 2014-561030 dated Jul. 7, 2016, 11 pages.
English Summary of Office Action for Korean Patent Application No. 10-2014-7027887 dated Mar. 8, 2016, 8 pages.
International Patent Application No. PCT/US14/23883, International Search Report, dated Jul. 10, 2014, 3 pages.
International Patent Application No. PCT/US14/23485, International Search Report, dated Jul. 7, 2014, 2 pages.
International Patent Application No. PCT/US14/24530, International Search Report, dated Jul. 15, 2014, 2 pages.
International Patent Application No. PCT/US14/24543, International Search Report, dated Jul. 28, 2014, 2 pages.
English Summary of the Office Action issued in corresponding Japanese Application No. 2022-135474, dated Aug. 25, 2023, 4 pages.
English Summary of Office Action for corresponding Japanese Patent Application No. 2021-017001 dated May 30, 2022, 2 pages.

(56) References Cited

OTHER PUBLICATIONS

Japanese Office Action dated Feb. 6, 2020 for Japanese Patent Application No. 2019-060748, 4 pages.
English Summary of Office Action for Japanese Application No. 2021-017001 dated Oct. 19, 2021, 6 pages.
Office Action for EP 13 757 994.2-1122; dated Jun. 18, 2021, 5 pages.
Communication from the European Patent Office for European Patent Application No. EP 13757994.2 dated Feb. 2, 2022 (7 Pages).
Extended European Search Report issued in corresponding Application No. EP 23220455.2, dated Mar. 14, 2024, 11 pages.
European Office Action, dated May 10, 2023, for the corresponding European Patent Application No. 13757994.2, 9 pages.
European Office Action, dated Dec. 12, 2022, for the corresponding European Patent Application No. 13757994.2, 9 pages.
English Summary of Office Action for Japanese Patent Application No. 2017-121208, 6 pages.

\* cited by examiner

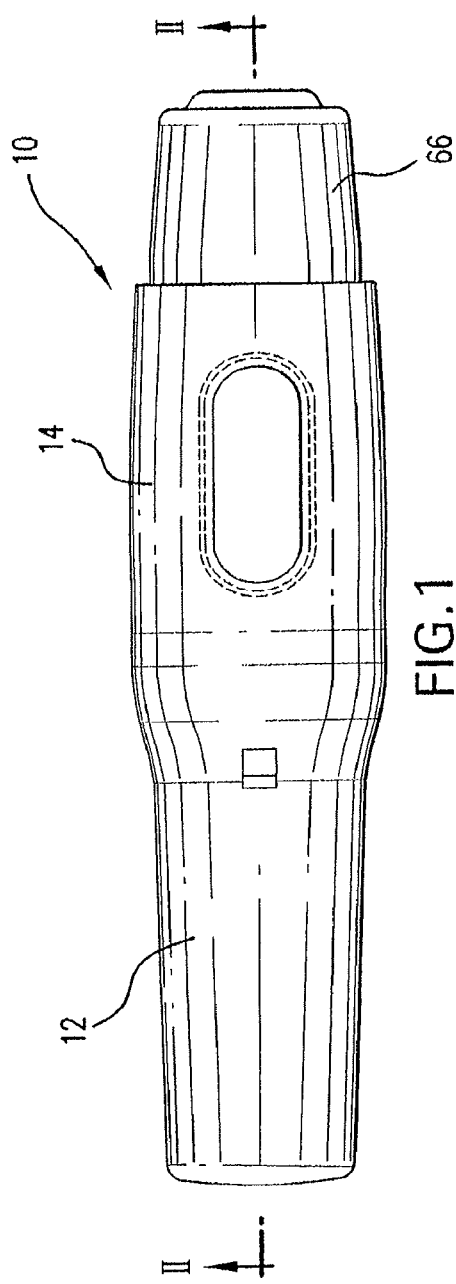
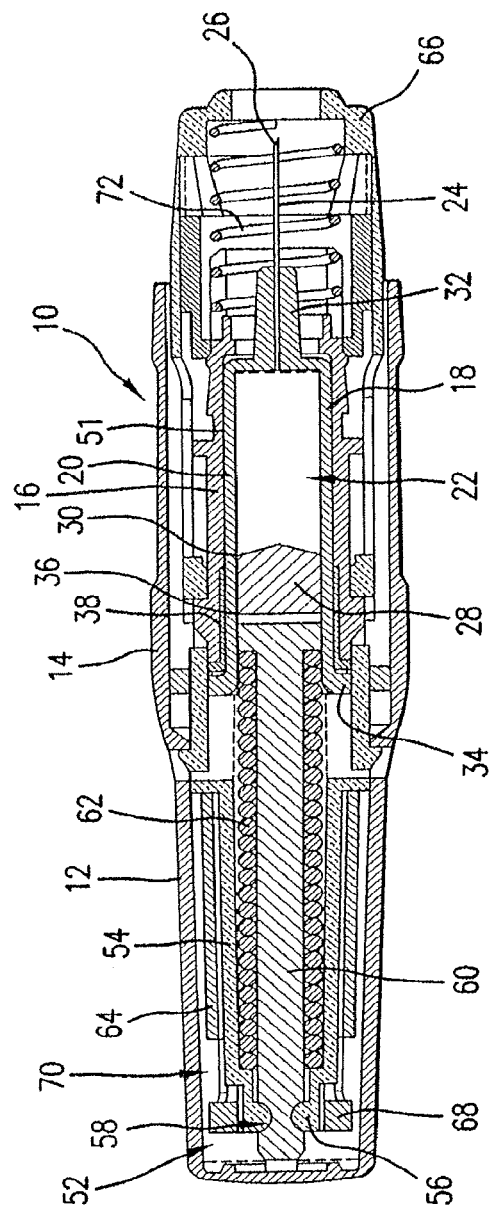
FIG. 1
FIG. 2

PREFILLED SYRINGE WITH BREAKAWAY FORCE FEATURE

CROSS REFERENCE TO RELATED APPLICATIONS

This application is a continuation of U.S. patent application Ser. No. 16/591,169 filed Oct. 2, 2019, which is a continuation of U.S. patent application Ser. No. 14/702,275 filed May 1, 2015, now U.S. Pat. No. 10,478,559, which is a continuation of U.S. patent application Ser. No. 13/785,582, filed Mar. 5, 2013, now U.S. Pat. No. 9,486,583 which claims the benefit of priority from U.S. Provisional Patent Application No. 61/607,339 filed Mar. 6, 2012, each of which are incorporated by reference herein for all purposes in their entirety.

BACKGROUND OF THE INVENTION

The present invention relates to a jet injector and in some embodiments a needle-assisted jet injector that uses a low jet injection pressure and has a lock ring that provides breakaway force resistance.

Certain jet injection devices have needle guards that must be retracted prior to insertion of the needle and triggering of the jet injection. A certain amount of force is normally required to trigger the jet injection. To assure sufficient needle guard travel for needle insertion and triggering, it is at times desirable to require a breakaway force prior to significant needle guard retraction to assure that insertion of the needle and triggering of triggering force is overcome. The present invention addresses this problem.

SUMMARY OF THE INVENTION

In certain embodiments, the invention relates to a jet injector. In one embodiment, the jet injector includes a prefilled syringe having a container portion defining a fluid chamber containing a medicament; an injection-assisting needle disposed at the distal end of the chamber, having an injecting tip configured for piercing an insertion location, and defining a fluid pathway in fluid communication with the chamber for injecting the fluid from the chamber into an injection site; a plunger movable within the fluid chamber; a housing that houses the prefilled syringe and is configured for allowing insertion of the needle at the injection location to an insertion point that is at a penetration depth below the surface, the housing including: a retractable guard that is movable between a protecting position in which the needle is disposed within the guard and an injecting position in which the tip of the needle is exposed for insertion to the insertion point, and an interference component adjacent to the retractable guard that interferes with the movement of the retractable guard when the retractable component is moved at least partially from the protecting position toward the injecting position; a syringe support supportively mounting the prefilled syringe in the housing; an energy source configured for biasing the plunger with a force selected to produce an injecting pressure on the medicament in the fluid chamber to jet inject the medicament from the fluid chamber through the needle to the injection site.

In certain embodiments, the energy source and prefilled syringe are configured such that the injecting pressure remains between about 80 p.s.i. and about 1000 p.s.i. during injection of the medicament. In one embodiment, the energy source and prefilled syringe are configured such that the injecting pressure remains below about 500 p.s.i. and above about 90 p.s.i. during the injection of the medicament. In another embodiment, the energy source and prefilled syringe are configured to produce the injecting pressure that remains at least at about 100 p.s.i. during the injection of the medicament. In one embodiment, the energy source and prefilled syringe are configured such that the injecting pressure remains up to about 350 p.s.i. during the injection of the medicament.

In certain embodiments, the prefilled syringe has a distal portion in which the injection-assisting needle is located, and a proximal portion opposite the distal portion; and the syringe support axially supports the proximal portion of the pre-filled syringe during the jet injection of the medicament, such that the distal portion of the prefilled syringe is substantially unsupported in an axial direction. In one embodiment, the container portion of the pre-filled syringe is made of blown glass. In another embodiment, the injection-assisting needle is adhered to the glass.

In certain embodiment, the interference component is a ring having at least one abutment arm extending distally from a proximal end dimensioned to fit within the housing, the abutment arm having at least one tapered portion. In one embodiment, the at least one abutment arm has an engagement portion axially adjacent to the at least one tapered portion that is configured to cause resistance to the movement of the retractable guard when the retractable guard is moved at least partially from the protecting position toward the injecting position.

In one embodiment, the energy source comprises a spring. In one embodiment, the jet injector further includes a ram that is biased by the spring against the plunger to produce the injecting pressure, wherein the ram comprises a bell portion on which the spring is seated, and the bell portion defines a hollow interior configured for receiving the prefilled syringe when the device is fired, such that the spring surrounds the prefilled syringe.

In some embodiments, the jet injector further includes a trigger mechanism operably associated with the energy source for activating the energy source to jet inject the medicament, wherein the trigger mechanism is configured for activating the energy source after the retractable guard is retracted from the protecting position. In one embodiment, the retractable guard is operably associated with the trigger mechanism to cause the trigger mechanism to activate the energy source when the guard is retracted to the injecting position.

In some embodiments, the interference component is a sleeve having an engagement portion extending outwardly from an outer surface of the sleeve that is configured to cause resistance to the movement of the retractable guard when the retractable guard is moved at least partially from the protecting position toward the injecting position. In other embodiments, the interference component is a latch coupled to the housing that is configured to cause resistance to the movement of the retractable guard when the retractable guard is moved at least partially from the protecting position toward the injecting position.

In certain embodiments, the housing is configured for allowing insertion of the needle to the penetration depth, which is between about 0.5 mm and about 5 mm below the surface at the insertion location.

In certain embodiments, the housing is configured for allowing insertion of the needle to the penetration depth, which is between about 11 mm and about 13 mm below the surface at the insertion location.

In certain embodiments, the chamber contains about between 0.02 mL and about 4 mL of the medicament.

In certain embodiments, the penetration depth and injecting pressure are sufficient to substantially prevent backflow of the injected medicament.

In other embodiments, the jet injector further includes a syringe cushion associated with the syringe support and prefilled syringe to compensate for shape irregularities of the pre-filled syringe.

In certain embodiments, the invention relates to a lock ring for a jet injector. In other embodiments, the lock ring includes at least one abutment arm extending distally from a proximal end of a body dimensioned to fit within in a housing of the jet injector, the abutment arm having at least one tapered portion and at least one engagement portion axially adjacent to the at least one tapered portion, the engagement portion being configured to cause resistance to the movement of a retractable guard of the jet injector; and at least one flap radially adjacent to the at least one abutment arm extending distally from the proximal end of the body.

BRIEF DESCRIPTION OF THE SEVERAL VIEWS OF THE DRAWINGS

The foregoing summary, as well as the following detailed description of embodiments of the present invention, will be better understood when read in conjunction with the appended drawings of exemplary embodiments. It should be understood, however, that the invention is not limited to the precise arrangements and instrumentalities shown.

In the drawings:

FIG. 1 is a side view of an embodiment of a jet injector constructed according to the present invention, showing the injector prior to injection;

FIG. 2 is a cross-sectional view of the jet injector of FIG. 1 thereof taken along plane II-II;

DETAILED DESCRIPTION OF THE INVENTION

With reference to the accompanying drawings, various embodiments of the present invention are described more fully below. Some but not all embodiments of the present invention are shown. Indeed, various embodiments of the invention may be embodied in many different forms and should not be construed as limited to the embodiments expressly described. Like numbers refer to like elements throughout. The singular forms "a," "an," and "the" include the singular and plural unless the context clearly dictates otherwise.

Figure 3:
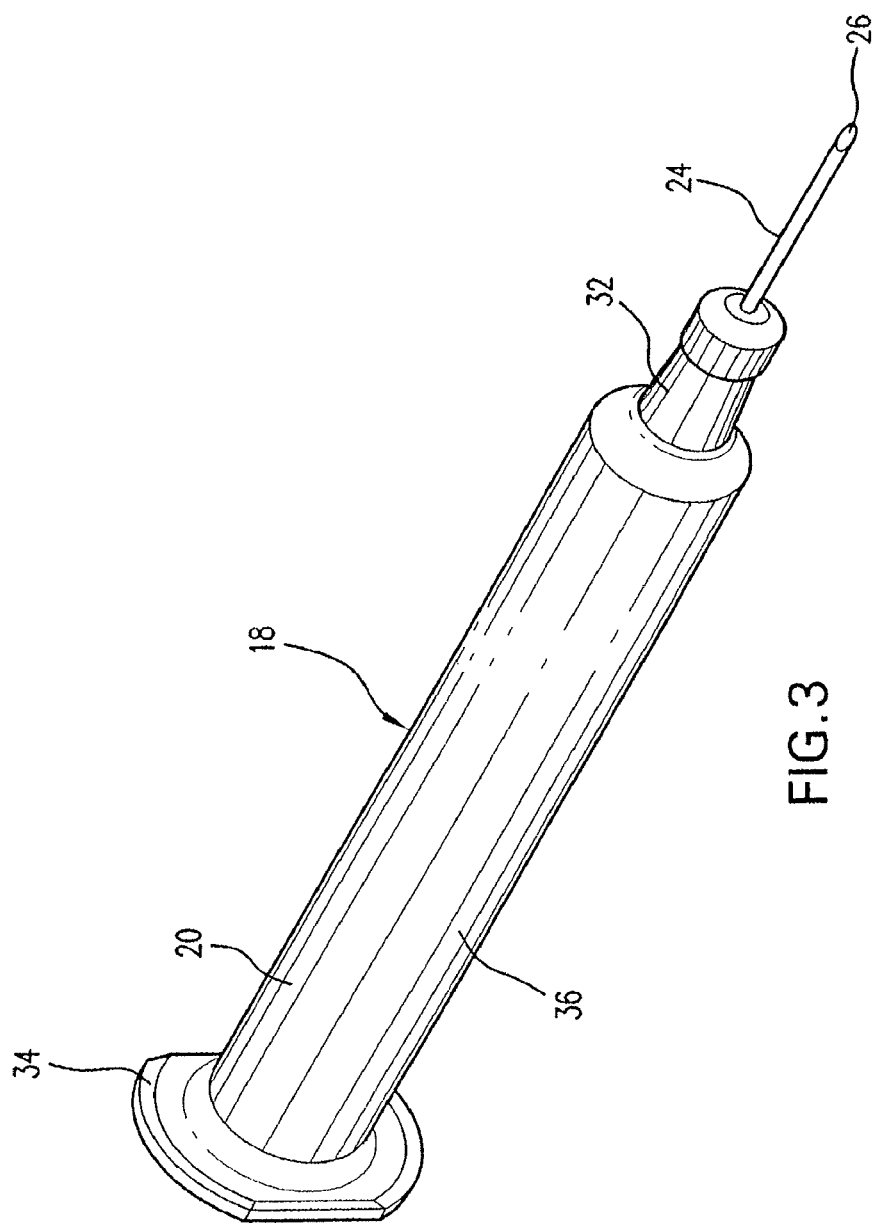
FIG. 3 is a perspective view of a prefilled syringe for use in the jet injector of FIG. 1.

Referring to FIGS. 1 and 2, an embodiment of an injector 10 has a housing 12 configured for allowing a user to handle the injector 10. The housing 12 includes an outer housing member 14 that substantially houses most of the components shown in FIG. 2. A syringe support member 16 is housed within and mounted with the housing 12. The syringe support member 16 is configured to hold and position a prefilled syringe 18, which is shown in FIG. 3. In one embodiment, the syringe support member 16 is substantially fixed to the housing 12, such as by snaps, an adhesive, a weld, or another known attachment. The prefilled syringe 18 has a container portion 20 that defines in its interior a fluid chamber 22, which is prefilled with medicament to be injected. At the distal end of the prefilled syringe 18 is an injection-assisting needle 24. Needle 24 has an injecting tip 26 configured as known in the art to penetrate the tissue of a patient, in certain embodiments, the skin of the patient. A needle bore extends through the needle 24, as known in the art. The bore is in fluid communication with the medicament in the fluid chamber 22 and is open at the needle tip 26 to inject the medicament.

At a proximal side of the fluid chamber 22, opposite from the needle 24, is a plunger 28 that seals the medicament in the fluid chamber 22. In certain embodiments, a syringe wall 30 comprises a tubular portion, in some embodiments closed at a distal end and open at a proximal end, to define the fluid chamber 22. Plunger 28 is slideably received in the tubular portion. The prefilled syringe 20 is configured such that when the plunger 28 is displaced in a distal direction, the volume of the fluid chamber 22 is decreased, forcing the medicament out therefrom and through the bore of the needle 24.

At the distal end of the fluid chamber 22 is a needle hub portion 32 to which the needle is mounted. In one embodiment, a syringe flange 34 extends radially from the proximal end of the syringe wall 30.

In one embodiment, the syringe 18 has a syringe body 36 that includes the flange 34, wall 30 and hub portion 32. In one embodiment, syringe body 36 that includes flange 34, wall 30, and hub portion 32 is of unitary construction. A preferred material for the syringe body 36 is glass, but other materials can be used in other embodiments. A suitable prefilled syringe is the BD Hypak™, which is available in various sizes and volumes and is sold prefilled with medicament. The glass of the syringe body 36 is adhered to the needle 24. Typical medicaments and medicament categories include epinephrine, atropine, sumatriptan, antibiotics, antidepressants, and anticoagulants. Using a prefilled syringe 18 facilitates handling of the medicament when the injector 10 is assembled, and there is an extensive body of knowledge of how the medicaments keep and behave in a prefilled syringe.

Figure 4:
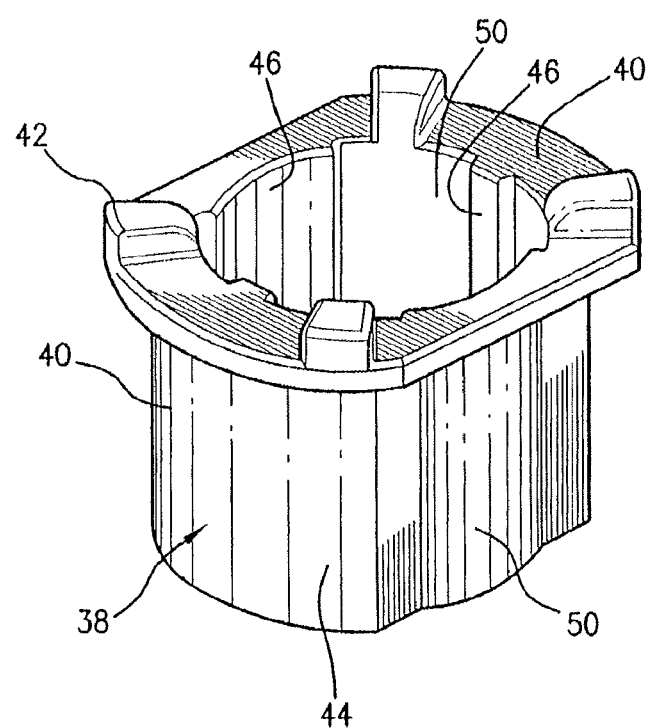
FIG. 4 is a perspective view of a syringe cushion of the jet injector of FIG. 1.

A syringe cushion 38, which is shown in detail in FIG. 4, is in certain embodiments made of an elastomeric material or other resilient material. A flange 40 of the syringe cushion 38 extends radially and is disposed and serves as an interface between the distal side of the syringe support member 16 and the syringe flange 34. Elevated portions, such as nubs 42 extend proximately from the cushion flange 40 and are configured and dimensioned to abut the syringe flange 34.

Prefilled syringes that are manufactured by a blown glass process can have significant dimensional tolerances and unevenness, particularly in the glass body 36. The cushion 38 can serve to accommodate the shape irregularities and to properly position and locate the prefilled syringe 18 within the syringe support 16. Typically, the axial thickness of glass blown syringe flanges on a 1 mL prefilled syringe is within about ±0.5 mm. For a BD Hypak™ 1 mL standard prefilled syringe, the thickness of the syringe flange 34 is 2 mm+0.5 mm or −0.4 mm, and in a 1 mL long configuration BD Hypak™ syringe, the flange axial thickness is about 1.65 mm±0.25 mm. Other dimensional variations that occur in typical glass prefilled syringes are in the internal and external diameters of the tubular wall 30. These variations can be accommodated by the resilient sleeve portion 44 of the syringe cushion 38, which extends axially around the interior of the syringe support 16. In one embodiment, the syringe cushion 38 is received in the interior of the syringe support member 16 and receives the syringe body 36, in certain embodiments fitting snugly therein.

In one embodiment, the sleeve portion 44 has radially inwardly extending protrusions 46 with a surface area and configuration selected to allow the insertion of the prefilled syringe 18 therein during assembly, but providing sufficient friction to maintain the syringe 18 in place and to provide cushioning and shock absorption during the firing of the injector 10. Outward protrusions 48 are also provided on the sleeve portion 44, which can be received in corresponding recesses of the syringe support 16 to prevent axial rotation therebetween. Recessed areas 50 can be provided on the interior and exterior of the syringe cushion 38 opposite corresponding protrusions 48 on the opposite radial side of the sleeve portion 44 if an increased wall thickness of the sleeve portion 44 is not desired. In an alternative embodiment one or both of the flange 40 and sleeve 44 of the syringe cushion 38 are substantially smooth, substantially without any protrusions. In one embodiment, the material and configuration of the syringe cushion 38 is also sufficient to entirely support the prefilled syringe 20 to withstand a firing force applied axially in a distal direction on the plunger 28. Thus, the entire support for the prefilled 20 can be provided on the syringe flange 34, while the distal end of the syringe 18 may itself be substantially unsupported in an axial direction. This can help withstand the shock on the glass body 36 of the prefilled syringe 20 produced by the elevated pressures within the fluid chamber 22.

To radially position the distal end of the prefilled syringe 18, the syringe support 16 in certain embodiments has a narrowed bore portion 51 that is in certain embodiments configured to abut the outside of the syringe wall 30. This is especially beneficial when the needle 24 is inserted into the patient's skin. The narrowed bore portion 51 can be made of a resilient material, such as an elastomer, or it can be made unitarily with the rest of the syringe support 16, in certain embodiments of a plastic material.

Referring to FIG. 2, in one embodiment, a trigger mechanism 52 is also housed within housing 12. The trigger mechanism 52 includes an inner housing 54 that can be attached to the outer housing 14, such as by snaps, an adhesive, a weld, or other known attachment. Trigger protrusions 56 extend inwardly from the proximal end of the inner housing 54 and are resiliently biased outwardly. Trigger protrusions 56 are received in a recess 58 of ram 60 in blocking association therewith to prevent distal movement of the ram 60 prior to the firing of the device. The ram 60 is urged towards the distal end of the injector 10 by an energy source, which in certain embodiments is a compression spring 52, although other suitable energy sources can alternative be used such as elastomer or compressed-gas springs. In one embodiment, the compression spring is a coil spring.

A trigger member of the trigger mechanism 52, such as a latch housing 64, is provided exterior to the inner housing to retain the trigger protrusions 56 in the blocking association in the recess 58 to prevent premature firing of the injector 10. The latch housing 64 is slideable inside the outer housing 14 with respect to the inner housing 54, in certain embodiments in an axial direction, and the latch housing 64 in certain embodiments surrounds the inner housing 54.

Figure 5:
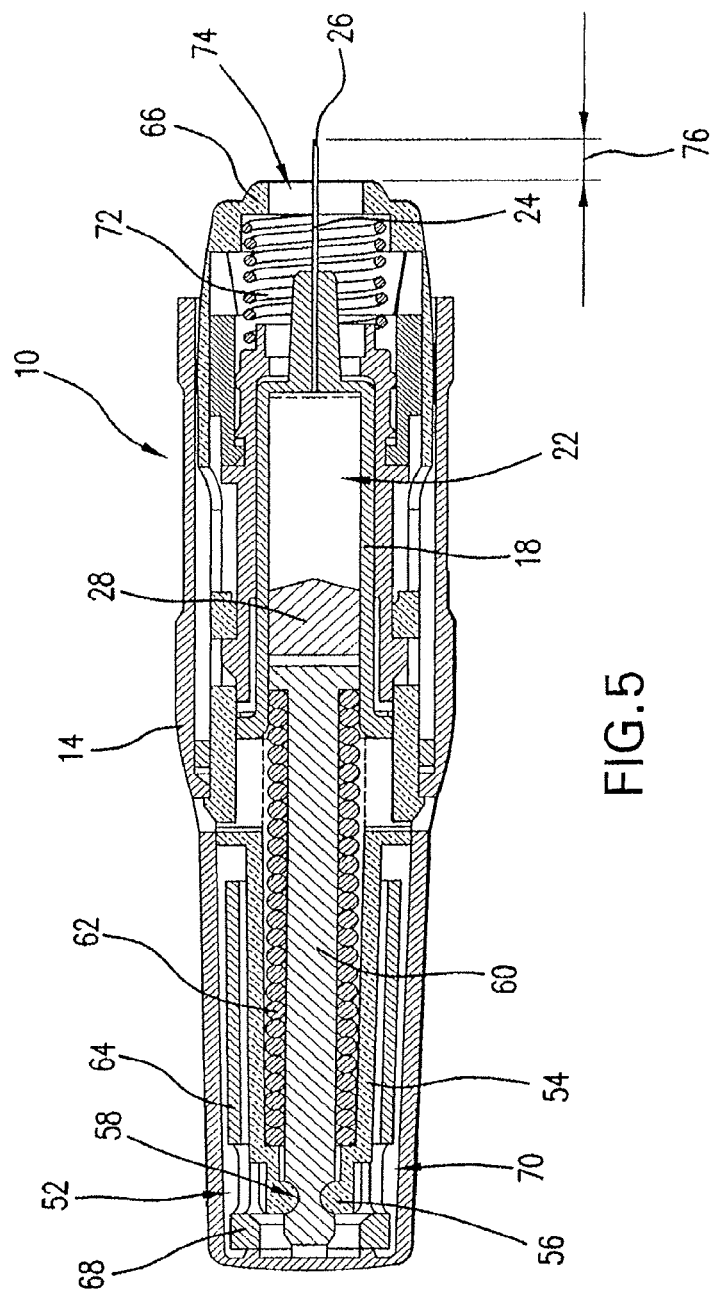
FIG. 5 is a cross-sectional view of the jet injector of FIG. 1, showing the injector at the start of the jet injection.

The housing 12 has a needle guard 66 that is moveable with respect to the outer housing 14. The needle guard 66 is shown in FIGS. 1 and 2 in a protecting position, in which the needle 24 is disposed within the guard 66. The needle guard 66 is retractable, in one embodiment into the outer housing 14, in a proximal direction to an injecting position, in which the needle tip 26 and an end portion of the needle 24 is exposed as shown in FIG. 5 for insertion into a patient. In one embodiment, the proximal movement of the guard is prevented substantially at the injecting position.

In one embodiment, an interference component 134 interferes with the movement of the needle guard when the needle guard is moved at least partially from the protecting position toward the injecting position.

Figure 10A:
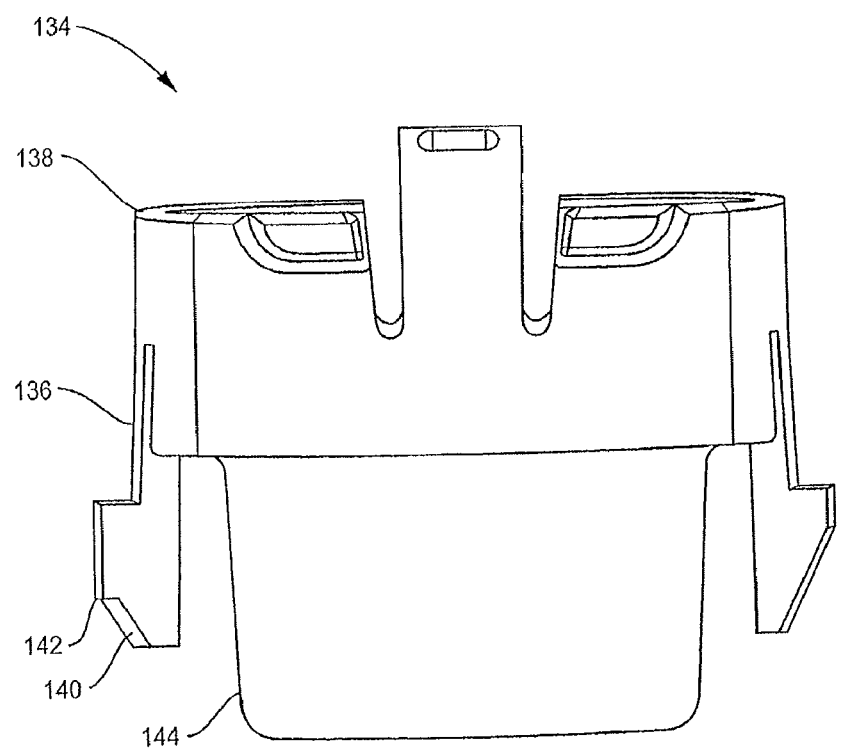
FIG. 10A is a side view of an interference component of a jet injector in accordance with an exemplary embodiment.
Figure 10B:
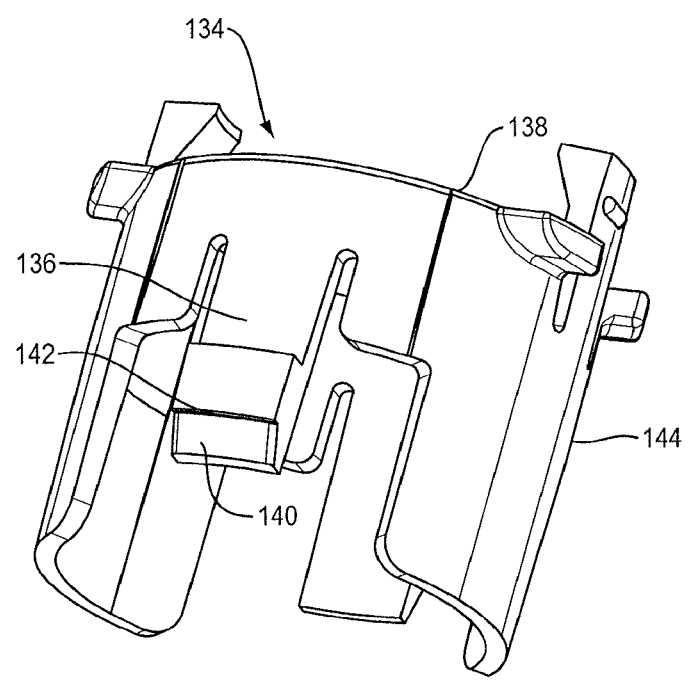
FIG. 10B is a perspective view of an interference component of a jet injector in accordance with an exemplary embodiment.

In one embodiment, the housing 12 has an interference component 134, e.g., a lock ring, adjacent to the needle guard 66, the interference component 134 interferes with the movement of the needle guard when the needle guard is moved at least partially from the protecting position toward the injecting position. Interference component prevents movement of the needle guard until the breakaway force 146 is exceeded. The interference component 134 is shown in FIGS. 10A and 10B. In one embodiment, the interference component 134 is included as part of a ring having at least one abutment arm 136 extending distally from a proximal end 138 dimensioned to fit within the housing 14, the abutment arm 136 having at least one tapered portion 140. The abutment arm 136 may also have an engagement portion 142 axially adjacent to the at least one tapered portion 140 that is configured to cause resistance to the movement of the needle guard 66 when the needle guard 66 is moved at least partially from the protecting position toward the injecting position. While interference component 134 may have more than one abutment arm 136 and correspondingly more than one engagement portion 142, certain embodiments include only one abutment arm 136 having an engagement portion 142. The interference component may also include at least one flap 144 radially adjacent to the at least one abutment arm 136 extending distally from the proximal end 138 of the interference component 134.

The interference component 134 may also be coupled to the housing 12, incorporated in a sleeve separate from the housing 12, or include a latch.

Figure 11:
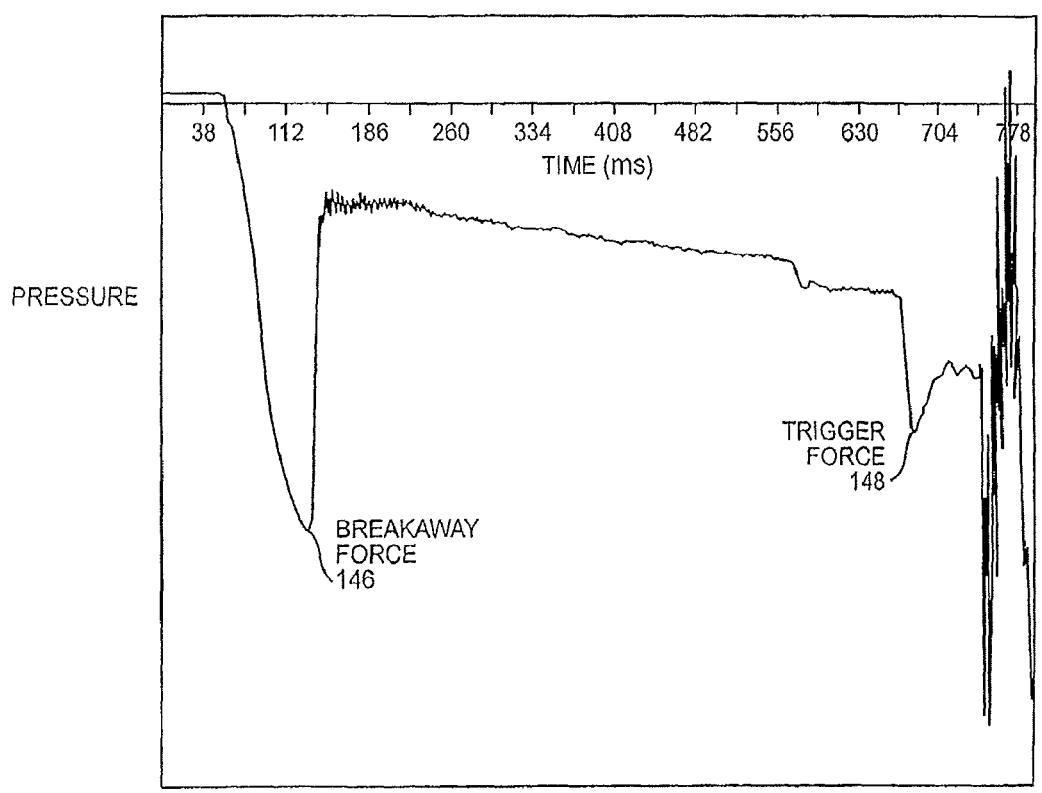
FIG. 11 is a graph showing the breakaway force over time of an jet injector in accordance with an exemplary embodiment.

Referring to FIG. 11, breakaway force 146 is needed to overcome the resistance on the needle guard 66 caused by the engagement portion 142 when the needle guard 66 is moved at least partially from the protecting position toward the injecting position. Referring to FIG. 11, breakaway force 146 is the resistance to retraction that is exerted on the needle guard 66 when an initial attempt to retract the needle guard 66 occurs. Breakaway force 146 is a distinct force from the triggering force 148 that is needed to cause jet injection of the medicament and is a greater force than that provided by the spring 62 that biases the needle guard 66 in the extended position. Breakaway force 146 is sometimes also a greater force than what occurs due to the friction of the needle guard 66 retracting motion sliding on other mating components in the device. In one embodiment the breakaway force 146 is controlled and only occurs as a single event.

Referring to FIG. 2, the needle guard 66 is associated with the latch housing 64 such that when the guard 66 is displaced distally it slides the latch housing 64 also in a distal direction to release the trigger protrusions 56 from the recess 58. In one embodiment, the latch housing 64 has a latching portion 68 that abuts the inner housing 54 in an association to bias and maintain the trigger protrusions 58 positioned in the blocking association with the ram 60 prior to the firing of the device 10. When the latch is slid proximately by the retracting of the guard 66 to the injecting position, the latching portion 68 slides beyond the portion of inner housing 54 that is contacts to flex the trigger protrusions 56 into the recess 58 of the ram 60, allowing the trigger protrusions 56 to move radially outwardly from the recess 58 and therefore from the blocking association. When this happens, spring 62 biases the ram 60 against plunger 28 to fire the jet injector 10. In certain embodiments, latch housing 64 defines trigger openings 70 adjacent to latching portions 68, which is configured to receive a portion of the inner housing 54, such as the surface disposed radially outwardly from the trigger protrusions 56.

In certain embodiments, the guard 66 is resiliently biased distally towards the protecting position by compression coil spring 72. Also, the needle guard 66 has an axial opening 74 to allow the needle 24 pass there through, and which may be sized according to the type of injector desired. The construction of the present embodiment allows a user to push the distal end of the injector 10 against the patient's skin, pushing the needle 24 into the skin at an insertion location, substantially at the same speed as the injector is pushed. Once the needle 24 is fully inserted to an insertion point at a penetration depth, the trigger mechanism 56 fires the jet injection to an injection site.

Referring to FIG. 5, in one embodiment, the prefilled syringe 18 and its needle 24 are not shuttled forward automatically into the patient's skin, such as by the firing energy source during the injection firing. The user preferably gently pushes the entire device forward to insert the needle 24, in certain embodiments retracting a guard against the skin in the process. In one embodiment, the prefilled syringe 18 is substantially stationary within the housing 12, and, in one embodiment, is substantially fixed thereto. In this manner, the present invention provides for a gentler treatment of the syringe during injection that enables the use of a sufficiently powerful spring 62 or other energy source to produce a jet injection without the risk of damaging the relatively fragile and complex shapes of the prefilled syringe, also allowing, for example, the injection of high viscosity solutions, where the risk of breaking a syringe, such as at the flange, is elevated in prior art injectors that shuttle the syringe forward in the housing and into the patient. Residual stresses are also often present in the glass bodies of prefilled syringes, and this configuration reduces the additional stresses imposed thereon during use, further protecting the syringe. Also, misalignments in the prefilled syringe are also rendered operationally less significant due to the gentle insertion of the needle that is possible with this configuration.

In one embodiment, the injecting position of the guard 66 is such that a predetermined length of the end of needle 24 is exposed from the guard 66. In some embodiments, such as where the opening 74 is of a sufficiently large diameter, the skin of the patient maybe allowed to extend into the opening 74 when the device 10 is pressed there against, and a needle that does not protrude beyond the distal end of the guard 66 can be used while still penetrating the skin to a certain depth. In most embodiments, the distance 76 by which the needle tip 26 extends past the distal end of the guard 66 will be fairly close to the depth of the insertion of the needle.

In one embodiment, such as for subcutaneous injection, the guard 66 is configured to allow insertion of the needle 24 to a penetration depth in the skin that is up to about 5 mm below the skin surface. In another embodiment, the penetration depth is less than about 4 mm, and in one embodiment is less than about 3 mm. In one embodiment, the insertion depth is at least about 0.5 mm and, in other embodiments, at least about 1 mm. In another embodiment, the distance 76 by which the needle extends past the guard 66 or the distal surface of the guard 66 that contacts the skin is up to about 5 mm, in one embodiment, up to about 4 mm, and in another embodiment up to about 3 mm. In certain embodiments, extension distance 76 is at least about 0.5 mm, in one embodiment at least about 1 mm, and in another embodiment at least about 2 mm. In one embodiment, tip 26 extends by a distance 76 of around 2.5 mm beyond the portion of the guard 66 that contacts the skin in the injecting position.

In another embodiment, such as for intramuscular injection, the injector is configured to allow the needle 24 to be inserted into the patient to a penetration depth in the skin, or alternatively beyond the distal surface of the guard, by a distance of up to about 15 mm. In one embodiment, this distance is about between 10 mm and 14 mm. In an embodiment for jet injection of epinephrine for instance, a penetration depth or distance beyond the guard is between about 11 mm and about 17.0 mm, and, in other embodiments, between about 13 to about 15 mm. Jet injection with this length needle improves the distribution of the medicament in the patient tissue compared to non jet injection. Other exposed needle lengths can be selected for jet injection to different depths below the skin, with, in certain embodiments, an overall penetration length of between about 0.5 mm and about 20 mm. In certain embodiments, the needle guard is configured for retracting from a protecting position, in one embodiment covering the entire needle 24 (See FIG. 2), to an injecting position, in which the desired length of the end of the needle 24 is exposed (See FIG. 5).

In some embodiments, the spring 62 and the prefilled syringe 18 are configured to jet inject the medicament. Thus, the spring 62 applies a force on the plunger 28 that is sufficient to elevate the pressure within the fluid chamber 22 to a level high enough to eject the medicament from the needle 24 as a jet. Jet injection is to be understood as an injection with sufficient velocity and force to drive the medicament to locations remote from the needle tip 26. In manual and autoinjector-type injections, in which the injection pressures are very low, the medicament exits the needle tip inside the patient and is typically deposited locally around the needle in a bolus. On the other hand, with the present jet injection device 10, the medicament is jet injected distally or in other directions, such as generally radially by the elevated pressure jet, which beneficially improves the distribution of the medicament after the injection and keeps a large bolus from forming that can detrimentally force the medicament to leak back out of the patient around the needle or through the hole left behind by the needle after it is removed.

Figure 6:
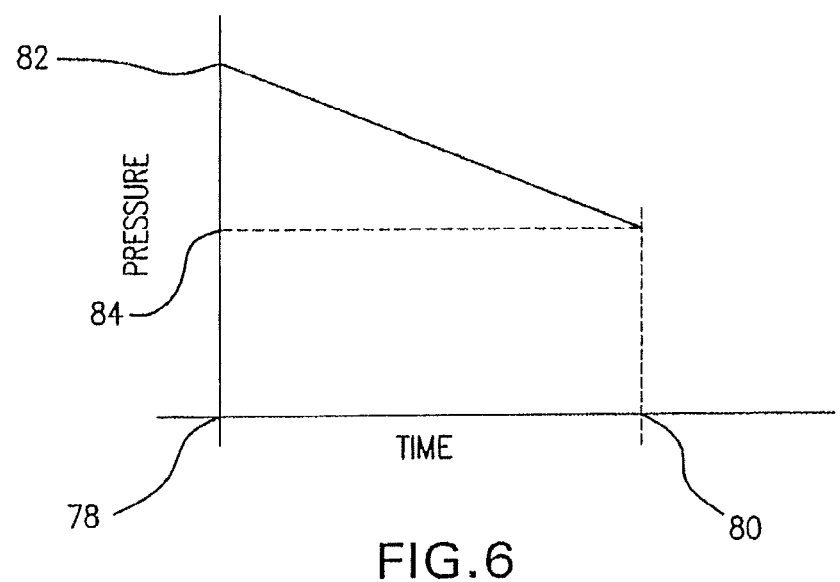
FIG. 6 is a graph showing the pressure present in the polluted chamber over time that contains medicament in an embodiment during jet injection.

Referring to the graph shown in FIG. 6, numeral 78 represents the point in time when device 10 is fired, and numeral 80 represents the point in time of completion of the medicament injection, in certain embodiments when the plunger 28 hits the forward wall of the container portion 20. Numeral 82 represents the initial and peak pressure during the injection, and numeral 84 represents the final and low pressure during the injection. Since the spring 62 of one embodiment has a linear spring constant and an injection-assisting needle is used to puncture the skin before commencing the injection, the pressure drops substantially linearly from the start of the injection 78 until the injection is completed. The final pressure 84 at the end 80 of the injection is sufficiently elevated so that even at the end of the firing stroke of ram 60, the medicament is still jet injected, and a very small amount or none of the medicament is deposited in a bolus around the needle tip 26.

In one embodiment, the peak pressure during the injection is less than about 1,000 p.s.i., in one embodiment less than about 500 p.s.i., and in another embodiment less than about 350 p.s.i. At the end 80 of the injection, the pressure 84 applied to the medicament in the fluid chamber 22 is in one embodiment at least about 80 p.s.i., in one embodiment at least about 90 p.s.i., and in another embodiment at least about 100 p.s.i. In one embodiment of the invention, the initial pressure 82 is around 330 p.s.i., and the final pressure is about 180 p.s.i., while in another embodiment the initial pressure 82 is about 300 p.s.i., dropping to around 110 p.s.i. at the end 80 of the injection. The needles used in these embodiments are between 26 and 28 gauge, and are in certain embodiments around 27 gauge, but alternatively other needle gages can be used where the other components are cooperatively configured to produce the desired injection. In an embodiment for jet injection of epinephrine for instance, certain embodiments of the needles are between 20 and 25 gauge, and in other embodiments, 22 gauge. In one embodiment, the components of the injector 10 are configured to jet inject the medicament to a subterraneous injection site.

The amount of medicament contained and injected from fluid chamber 22 is in one embodiment between about 0.02 mL and about 4 mL, in certain embodiments less than about 3 mL, and in other embodiments is around 1 mL. Larger volumes may also be selected depending on the particular medicament and dosage required. In one embodiment, the prefilled syringe is assembled into the remaining parts of the jet injector 10 already containing the desired amount of medicament. In one embodiment, the prefilled syringe contains about 1 mL of medicament.

In one embodiment, injection rates are below about 0.75 mL/sec., in one embodiment preferably below about 0.6 mL/sec., in one embodiment at least about 0.2 mL/sec., in one embodiment at least about 0.3 mL/sec, and in other embodiments at least about 0.4 mL/sec. In one embodiment, the injection of the entire amount of medicament is completed in less than about 4 seconds, in one embodiment in less than about 3 seconds, and in other embodiments in less than about 2.5 seconds. In one embodiment, the medicament injection takes at least about 1 second, in one embodiment at least 1.5 seconds, and in other embodiments at least about 1.75 seconds. In one embodiment, the injector 10 injects the medicament at about 0.5 mL/sec., completing the injection of 1 mL in about 2 seconds.

U.S. Pat. No. 6,391,003 discloses several experimental results of pressures that can be applied to medicament in a glass cartridge, using 26 and 27 gauge needles. The following table illustrates injections with different peak pressures that can be used with glass prefilled syringes:

| Pressure and Time (sec.) to Inject 1 cc | | |
|---|---|---|
| Pressure | 26 Gauge needle | 27 Gauge needle |
| 150 p.s.i. | 2.1 | 4.2 |
| 200 p.s.i. | 1.9 | 3.9 |
| 240 p.s.i. | 1.7 | 3.3 |
| 375 p.s.i. | 1.4 | 3.1 |

It is foreseen that higher pressures and flow rates will be used with shorter needle penetration into the patient skin to achieve jet injections to a particular desired depth substantially without medicament leakback.

It has been found that using the jet injection of the present device, short needles can be used to inject medicament to different parts of the skin, in certain embodiments subcutaneously, substantially without any leakback. Using a needle 24 that extends by about 2.5 mm from the needle guard 66, a 27 gauge needle 24, and a pressure in the fluid chamber 22 peaking at around 300 p.s.i. and ending at around 100 p.s.i., resulting in a flow rate of about 0.5 mL/sec., 1 mL of medicament has been found to successfully be injected without leakback in close to 100% of the tested injections. Thus, the needle-assisted jet injector 10 of the present invention permits jet injection of the medicament using a very short needle reliably regardless of the thickness of the patient's skin or the patient's age, weight or other typical factors that complicate non-jet injecting with short needles.

Figure 7:
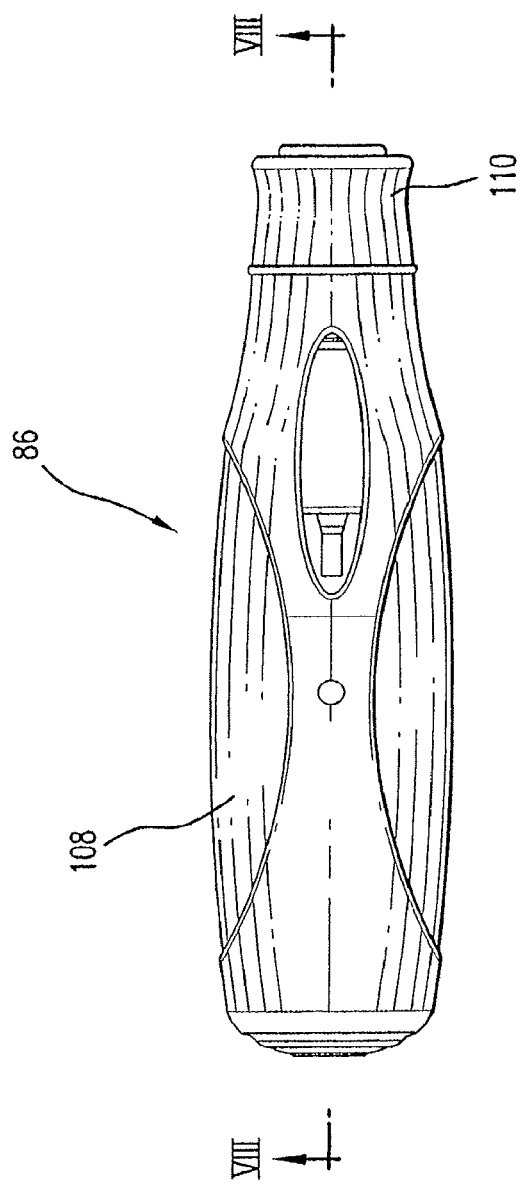
FIG. 7 is a side view of another embodiment of an injector that is configured for using a narrow diameter prefilled syringe.
Figure 8:
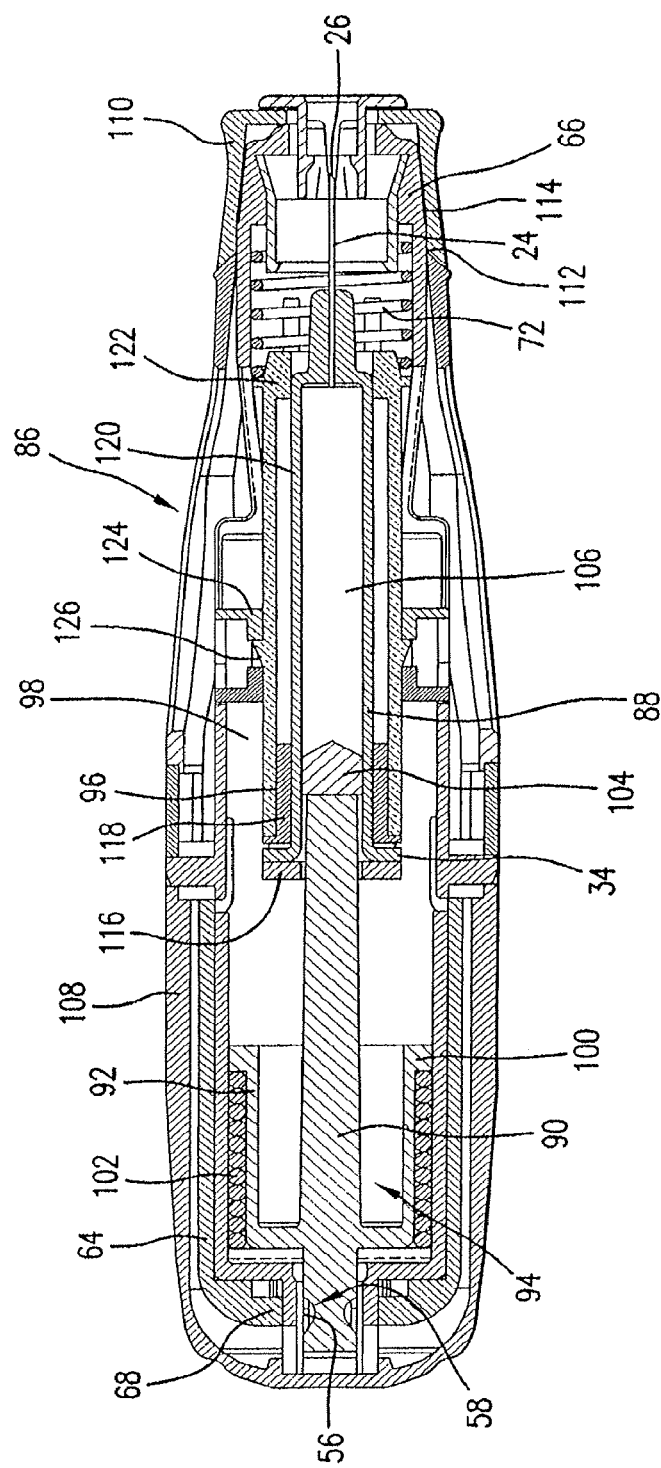
FIG. 8 is a cross-sectional view of the jet injector of FIG. 1; taken along plane VIII-VIII.

FIGS. 7 and 8 show another embodiment of the present invention that uses a prefilled syringe that has a long, but smaller-diameter configuration than the embodiment of FIG. 2. While in the embodiment of FIG. 2, the firing spring 62 extends into the bore of the prefilled syringe 18 during the firing stroke, the narrower prefilled syringe 88 of injector 86 does not provide as much space to accommodate a spring. Consequently, the ram 90 of injector 86 includes a bell portion 92 defining a hollow interior 94 that is configured to receive the proximal end of the prefilled syringe 88 and the syringe support 96 when the injector 86 is fired. Similarly, a bell-receiving space 98 is defined around the exterior of the prefilled syringe 88 and syringe support 96 to receive the bell portion 92 during the firing. The bell portion 92 includes a spring seat 100 extending radially outwardly and configured and disposed to seat a compression spring 102. When the trigger mechanism 56 is activated and the device 86 is fired, spring 102 acts against seat 100 to drive the ram 90 against plunger 104 to jet inject the medicament from the fluid chamber 106. As a result, after firing, the spring 102 radially surrounds the prefilled syringe 88. The outer housing portion 108 is wider than outer housing portion 14 of injector 10 to accommodate the bell portion 92 and larger diameter spring 102.

One available long configuration syringe with a 1 mL capacity has a cylindrical syringe body portion with a diameter of 8.15 mm, which would in certain embodiments be used in the injector of FIGS. 7 and 8, while one available shorter configuration syringe of the same capacity has a cylindrical syringe body portion with a diameter of 10.85 mm, which would in certain embodiments be used in the injector of FIGS. 1 and 2. While the embodiment with a bell portion 92 can be used with wider/shorter syringes, in certain embodiments, the prefilled syringes have an outer diameter cylindrical wall of less than about 10 mm, and in other embodiments less than about 9 mm.

Injector 86 also includes a cap 110 fitted around the needle guard 66, and associated with the outer housing 108 to prevent retraction of the needle guard 66 and the triggering of the device 86. Additionally, the cap 110 seals off the needle tip 26 and can be removed prior to using the device 86. In one embodiment, the cap 110 is configured to fit over the needle guard 66 in a snap-fit association therewith, such as by including a narrower diameter portion 112 associated with an enlarged diameter portion 114 of the needle guard 66.

Additionally, injector 86 employs a syringe cushion cap 116 that extends around the outside of the syringe flange 34 from the syringe cushion 118 to help trap and retain the prefilled syringe 88. In one embodiment, a cushion cap 122 is connected to the cushion 118 and is, in certain embodiments, of unitary construction therewith. The cushion cap 122 abuts the distal end of the syringe body 120 to radially position and hold the proximal end of the body 120 while the needle 24 is being inserted into the patient. Similarly to the embodiment of FIG. 2, the syringe holder 96 is associated with the housing in a substantially fixed position, such as by mounting portion 124, which traps protrusions 126 of the syringe holder.

Figure 9:
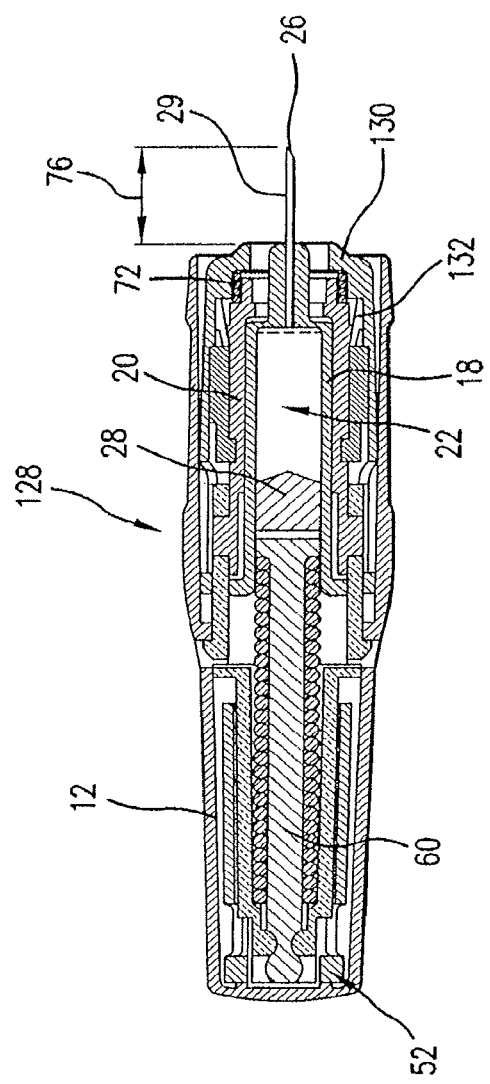
FIG. 9 is a cross-sectional view of another embodiment of an injector using a needle for intramuscular jet-injection.

Referring to FIG. 9, injector 128 has a needle guard 130 configured to retract further into the injector housing than the injector of FIGS. 1 and 2 or FIG. 5 before the trigger mechanism 52 fires the jet injection. The injector in this figure is shown in a position in which the trigger mechanism 52 is being released and about to fire the injection. The distance 76 by which the needle extends past the guard 130 or the distal surface of the guard 130 that contacts the skin in certain embodiments between about 12.5 and 13 mm. In one embodiment, the guard is preferably configured to reextend to a protecting position after the device is fired and removed from the patient, such as under the bias of spring 72, and is locked in that position by locking members 132, as known in the art to prevent reuse on the injector.

In other embodiments, the guard length, the location of the guard injecting position with respect to the needle tip (including the guard throw between the protecting and injecting positions), and the length of the needle from the syringe body can be selected to allow for shallower or deeper needle insertions before the device is fired, providing lesser or greater distances 76, respectively. In one embodiment, the guard is kept from sliding further back than substantially at the firing position, to better control in insertion depth into the patient.

Each and every reference herein is incorporated by reference in its entirety. The entire disclosure of U.S. Patent Application 2011/0144594, U.S. Pat. Nos. 8,021,335 and 6,391,003 are hereby incorporated herein by reference thereto as if fully set forth herein.

While illustrative embodiments of the invention are disclosed herein, it will be appreciated that numerous modifications and other embodiments may be devised by those skilled in the art. For example, the features for the various embodiments can be used in other embodiments, such as the needle and guard cap of FIGS. 7 and 8, which can be applied to the embodiment of FIG. 1. Therefore, it will be understood that the appended claims are intended to cover all such modifications and embodiments that come within the spirit and scope of the present invention.

What is claimed is:

1. An injector, comprising:
a housing;
a prefilled syringe containing a volume of a medicament disposed within the housing, the prefilled syringe having a needle coupled to and extending from a distal end thereof;
a retractable guard disposed at least partially within the housing and axially moveable relative thereto; and
an interference component disposed within the housing and configured to cause resistance to axial movement of the retractable guard when the retractable guard is moved proximally relative to the housing,
wherein a breakaway force is configured to be applied to the retractable guard to overcome the resistance by the interference component,
wherein a triggering force is configured to be applied to the retractable guard to initiate delivery of the medicament, and
wherein the breakaway force is equal to or greater than the triggering force.

2. The injector of claim 1 further comprising:
a syringe support supportively mounting the prefilled syringe in the housing,
wherein the prefilled syringe has a distal portion in which the needle is located, and a proximal portion opposite the distal portion, and
wherein the syringe support axially supports the proximal portion of the prefilled syringe such that the distal portion of the prefilled syringe is substantially unsupported in an axial direction.

3. The injector of claim 2, wherein the prefilled syringe is made of glass.

4. The injector of claim 3, wherein the needle is coupled to the glass.

5. The injector of claim 1 further comprising:
a plunger moveable within a fluid chamber of the prefilled syringe; and
an energy source configured to bias the plunger with a force selected to produce an injecting pressure on a medicament in the fluid chamber to expel the medicament through the needle.

6. The injector of claim 5 further comprising:
a ram that is biased by the energy source against the plunger to produce the injecting pressure, the ram comprising a bell portion on which the energy source is seated,
wherein the prefilled syringe defines a hollow interior configured to receive at least a portion of the ram and energy source when the injector is fired.

7. The injector of claim 5 further comprising:
a trigger mechanism operably associated with the energy source for activating the energy source to expel the medicament, the trigger mechanism configured to activate the energy source after the retractable guard is moved proximally relative to the housing.

8. The injector of claim 7, wherein the retractable guard is moveable relative to the housing between a protecting position in which the needle is disposed within the retractable guard and an injecting position where the needle is at least partially exposed, and
wherein the retractable guard is operably associated with the trigger mechanism to cause the trigger mechanism to activate the energy source when the guard is retracted to the injecting position.

9. The injector of claim 1, wherein the prefilled syringe contains about between 0.02 mL and about 4 mL of the medicament.

10. The injector of claim 1, wherein delivery of the medicament is at a penetration depth and an injecting pressure sufficient to substantially prevent backflow of the medicament from a subject.

11. The injector of claim 1, wherein the interference component includes at least one abutment arm, the at least one abutment arm having at least one tapered portion and an engagement portion axially adjacent to the at least one tapered portion, and wherein the engagement portion is configured to resist the movement of the retractable guard when the retractable guard is moved proximally relative to the housing.

12. The injector of claim 11, wherein the interference component further comprises:

a second abutment arm including a second abutment arm tapered portion and a second abutment arm face.

13. The injector of claim 12, wherein the at least one abutment arm includes a first abutment arm face and the first abutment arm face is longer axially than the second abutment arm face.

14. The injector of claim 12, wherein the at least one abutment arm includes a face adjacent to the engagement portion.

15. The injector of claim 12, wherein the second abutment arm face is adjacent to the second abutment arm tapered portion.

16. The injector of claim 12, wherein the second abutment arm tapered portion is longer axially than the at least one tapered portion.

17. The injector of claim 1, wherein the breakaway force is greater than a frictional force from friction between the retractable guard and the interference component as the retractable guard is moved proximally relative to the housing.

18. The injector of claim 1, wherein the breakaway force is applied during an initial proximal movement of the retractable guard relative to the housing.

19. The injector of claim 1, wherein the interference component is coupled to the housing.

20. The injector of claim 1, wherein the interference component is a latch.

21. The injector of claim 1, wherein the medicament is epinephrine.

* * * * *